US011345884B2

(12) United States Patent
Jin

(10) Patent No.: US 11,345,884 B2
(45) Date of Patent: May 31, 2022

(54) BIOCOMPATIBLE CONDITIONED CELL MEDIUM COMPOSITIONS AND USES THEREOF

(71) Applicant: Cellum Biomedical, Inc., Irvine, CA (US)

(72) Inventor: Richard C. Jin, Murrieta, CA (US)

(73) Assignee: Cellum Biomedical, Inc., Irvine, CA (US)

(*) Notice: Subject to any disclaimer, the term of this patent is extended or adjusted under 35 U.S.C. 154(b) by 78 days.

(21) Appl. No.: 16/497,177

(22) PCT Filed: Apr. 2, 2018

(86) PCT No.: PCT/US2018/025655
§ 371 (c)(1),
(2) Date: Sep. 24, 2019

(87) PCT Pub. No.: WO2018/183998
PCT Pub. Date: Oct. 4, 2018

(65) Prior Publication Data
US 2020/0095539 A1 Mar. 26, 2020

Related U.S. Application Data

(60) Provisional application No. 62/479,733, filed on Mar. 31, 2017.

(51) Int. Cl.
*C12N 5/00* (2006.01)
*A61K 9/16* (2006.01)
(Continued)

(52) U.S. Cl.
CPC .............. *C12N 5/0018* (2013.01); *A61K 9/06* (2013.01); *A61K 9/1658* (2013.01); *A61K 47/36* (2013.01);
(Continued)

(58) Field of Classification Search
None
See application file for complete search history.

(56) References Cited

U.S. PATENT DOCUMENTS

| 5,656,450 A | 8/1997 | Boyan et al. |
| 6,179,872 B1 | 1/2001 | Bell et al. |
| (Continued) | | |

FOREIGN PATENT DOCUMENTS

| CN | 1376067 A | 10/2002 |
| CN | 1586636 A | 3/2005 |
| (Continued) | | |

OTHER PUBLICATIONS

Osugi, Masashi; et al; "Conditioned Media from Mesenchymal Stem Cells Enhanced Bone Regeneration in Rat Calvarial Bone Defects" Tissue Engineering; Part A, 18, 1479-1489, 2012 (Year: 2012).*

(Continued)

*Primary Examiner* — David W Berke-Schlessel
(74) *Attorney, Agent, or Firm* — Foley Hoag LLP

(57) ABSTRACT

The present invention is drawn, in part, to biocompatible compositions comprising a biocompatible polymer matrix and conditioned cell medium comprising i) a cell culture medium and ii) one or more agents synthesized by and secreted from one or more cells cultured in the cell culture medium, as well as therapeutic uses thereof, particularly in modulating bone and/or gum tissue growth.

28 Claims, 5 Drawing Sheets

(51) Int. Cl.
  *C12N 5/071* (2010.01)
  *C12N 5/077* (2010.01)
  *A61K 9/06* (2006.01)
  *A61K 47/36* (2006.01)

(52) U.S. Cl.
  CPC ......... *C12N 5/0625* (2013.01); *C12N 5/0654* (2013.01); *C12N 2501/105* (2013.01); *C12N 2501/11* (2013.01); *C12N 2501/115* (2013.01); *C12N 2501/117* (2013.01); *C12N 2501/12* (2013.01); *C12N 2501/13* (2013.01); *C12N 2501/135* (2013.01); *C12N 2501/148* (2013.01); *C12N 2501/15* (2013.01); *C12N 2501/155* (2013.01); *C12N 2501/165* (2013.01); *C12N 2501/19* (2013.01); *C12N 2501/22* (2013.01); *C12N 2501/2301* (2013.01); *C12N 2501/2306* (2013.01); *C12N 2501/2308* (2013.01); *C12N 2501/25* (2013.01); *C12N 2502/1142* (2013.01); *C12N 2502/1323* (2013.01)

(56) References Cited

U.S. PATENT DOCUMENTS

| 6,372,494 | B1 | 4/2002 | Naughton et al. |
|---|---|---|---|
| 2004/0142861 | A1 | 7/2004 | Mansbridge |
| 2011/0129447 | A1 | 6/2011 | Meretzki et al. |
| 2020/0095539 | A1 | 3/2020 | Jin |

FOREIGN PATENT DOCUMENTS

| CN | 101815531 A | 8/2010 |
|---|---|---|
| CN | 106039407 A | 10/2016 |
| JP | 2004/269477 A | 9/2004 |
| JP | 2004/534049 A | 11/2004 |
| WO | WO-00/69449 A2 | 11/2000 |
| WO | WO-2009/025730 A1 | 2/2009 |
| WO | WO-2016/201154 A1 | 12/2016 |

OTHER PUBLICATIONS

Peng, Chao; et al; "Culture media conditioned by heat-shocked osteoblasts enhances the osteogenesis of bone marrow-derived mesenchymal stromal cells" Cellular Biochemistry and Function, 25, 267-276; 2007 (Year: 2007).*

Seo, Young-JOng; et al; "The Effect of Fibroblast Growth Factor and Periodontal Ligament Fibroblast-Conditioned Medium on Fibroblast-Related Gene Expression in Bone Marrow Stromal Cells" Tissue Engineering and Regenerative Medicine, 10, 176-182, 2013 (Year: 2013).*

Zhang, Lian-Fang; et el; "Osteoblast-Secreted Factors Promote Proliferation and Osteogenic Differentiation of Bone Marrow Stromal Cells via VEGF/Heme-Oxygenase-1 Pathway" PLOS One, 9, e99946, 2014 (Year: 2014).*

International Search Report and Written Opinion for International Application No. PCT/US18/25655 dated Jun. 21, 2018.

Tao et al., "Hard Tissue Engineering Material Osseointegration Evaluation Method and Application," International Journal of Orthopedic Science (2013).

* cited by examiner

BIOCOMPATIBLE CONDITIONED CELL MEDIUM COMPOSITIONS AND USES THEREOF

CROSS-REFERENCE TO RELATED APPLICATIONS

This application claims the benefit of U.S. Provisional Application No. 62/479,733, filed on 31 Mar. 2017; the entire contents of said application are incorporated herein in their entirety by this reference.

FIELD OF THE INVENTION

The field of the invention is cell culture, periodontal and bone applications, and medical biotechnology, particularly biocompatible compositions comprising a polymer matrix infused with conditioned cell media generated from cultured cells. Cultured cells comprising any variety of cells, such as fibroblasts and osteoblasts, are grown in vitro in cell medium, and in the course of culture, the cultured cells synthesize and secrete agents into the cell medium. The cell medium containing agents are collected and combined with polymer matrix to generate biocompatible compositions and pharmaceutical preparations. The compositions and preparation can be used for regenerative processes, including but not limited to, regenerating bone, gum, or tissue; promoting bone growth; rejuvenating skin cells and tissue; stimulating wound healing; and treating dental-related diseases, disorders, and conditions, such as periodontal and gum disease.

BACKGROUND OF THE INVENTION

Periodontal disease, ranging from gingivitis to more severe forms of periodontitis, remains a significant health problem and is a major cause of tooth loss in adults both in the United States and throughout the world (E. Reich et al. (1993) *Comm. Dent. Oral Epidem.* 21:379; J. Angelillo et al. (1996) *Comm. Dent. Oral Epidem.* 24:336; H. Murray et al. (1997) *Int. Dent. J.* 47:3-8; R. C Oliver et al. (1998) *J. Periodontol.* 69:269-278; G. Ong (1998) *Int. Dental J.* 48:233-238; I. Haddad et al. (1999) *Dental J.* 49:343-346; E. F. Corbet et al. (2000) *Periodontol.* 29:122-152; A. Sheiham et al. (2000) *Periodontol.* 29:104-121; I. Chestnutt et al. (2000) *J. Dentist.* 28:295-297; U. M. Irfan et al. (2001) *J. Int. Acad. Periodontol.* 3:14-21). It is estimated that different types of periodontal disease affect 15-35% of the U.S. population, which translates into tens of millions of patients (J. M. Albandar et al. (1999) *J. Peridontol.* 70:13-29) and costs billions of dollars a year. Furthermore, periodontal disease has implications beyond the deleterious effects on oral tissues and structural integrity, and represents a potential risk factor for increased morbidity and mortality for several systemic conditions including cardiovascular diseases, pregnancy complications and diabetes (R. C. Page et al. (1998) *Ann. Periodontol.* 3:108-120; R. I. Garcia et al. (1998) *Ann. Periodontol.* 3:339-349).

Periodontitis is an infectious disease in which an inflammatory process is stimulated by the presence of plaque that can lead to loss of clinical attachment and alveolar bone. The most common form of periodontal disease is observed in adults and shows chronic progression (I. Brook (2003) *Gen. Dent.* 51:424-428). The progression of periodontal disease relies on persistence of chronicity of the host response. Out of the hundreds of bacterial species present in the oral cavity, only a small number are involved in the etiology of periodontal disease (S. S. Socransky et al. (2002) *Periodontal.* 28:12-55). The biofilm can contain bacteria, such as *Porphyromonas gingivalis, Bacteroides forsythus*; and *Treponema denticola*, the presence of which is strikingly related to clinical features of periodontal disease, in particular the pocket depth and bleeding on probing (S. S. Socransky et al. (1998) *J. Clin. Periodontol.* 25:134-144). Some of these pathogenic organisms can invade periodontal tissues, dentinal tubules, as well as other areas of the oral cavity. Conventional periodontal therapy has emphasized mechanical removal of soft and hard accretions of bacteria from the root surface via use of dental instruments placed into the gingival crevice to mechanically shear the accretions from the tooth structure. However, scaling and root planning is often only partially effective in the removal of these accretions. Moreover, even in the case of easily accessible areas, the removal is transient and the bacteria re-colonize the root surface.

When virulent bacteria begin to flourish in the periodontal region, they release toxic and pathogenic products under the gum-line that induce an inflammatory response and can cause a chronic infection. As the bacterial toxins dissolve the alveolar bone, the gums and bone can recede together, exposing the roots of the teeth. In other instances, the bone can recede but the gums remain puffy and form a wall around the pockets of debris that have replaced the lost bone. In both circumstances, the roots of the teeth become exposed to either air or to irritating bacterial toxins, both of which can cause spontaneous pain or tooth sensitivities to cold, hot or sweet or sour food. Although the damage caused by bone loss is usually permanent, early periodontitis can be arrested with proper home oral hygiene and the risk of tooth loss is minimal. As bone loss progresses, more aggressive treatment must be performed to keep the teeth clean. If bone loss continues and the tooth support is compromised, the teeth become mobile and eventually are lost or need to be extracted.

Current treatment of periodontal diseases involves primarily the use of compositions containing antimicrobial compounds or various non-steroidal anti-inflammatory agents (NSAIDs). Systemic antibiotics have been used in the periodontal therapy (R. J. Genco (1981) *J. Periodontal.* 52:545-558). However, systemic delivery (e.g., oral or intramuscular) typically does not provide a sufficient concentration of antibiotics over an extended period of time to the gingival crevice area. In advanced cases of periodontal disease, surgical intervention to eliminate the periodontal pocket and recontour the bone can be performed. Splinting of loose teeth and selective reshaping of tooth surfaces to eliminate traumatic occlusion can be necessary. Despite these known treatments, there remains a need for improved compositions and methods for preventing and treating periodontal diseases. In particular, methods for preventing and treating periodontitis-related bone loss are highly desirable.

SUMMARY OF THE INVENTION

The present invention is based, at least in part, on the discovery that conditioned cell medium can be combined with a polymer matrix (e.g., agarose) to generate biocompatible compositions and pharmaceutical preparations for regenerative uses.

In one aspect, a biocompatible composition comprising (a) a biocompatible polymer matrix and (b) a conditioned cell medium comprising i) a cell culture medium and ii) one or more agents synthesized by and secreted from one or more cells cultured in the cell culture medium, is provided.

Numerous embodiments are further provided that can be applied to any aspect of the present invention and/or combined with any other embodiment described herein. For example, in one embodiment, the cells are fibroblasts, such as dermal fibroblasts and especially neonatal dermal fibroblasts. In another embodiment, the cells are osteoblasts. In still another embodiment, the cells are fibroblasts and osteoblasts. In yet another embodiment, the cells are a co-culture of fibroblasts and osteoblasts. In another embodiment, the cells are actively proliferating cells. In still another embodiment, the cell culture medium comprises a basal cell culture medium and further comprises one or more supplements selected from the group consisting of fetal bovine serum (FBS), L-glutamine, human epidermal growth factor (EGF), basic fibroblast growth factor (bFGF), and ascorbic acid. In yet another embodiment, the basal cell culture medium is Dulbecco's modified eagle medium (DMEM). In another embodiment, the supplement is a recombinant growth factor, such as a human recombinant growth factor. In still another embodiment, the one or more agents comprises a growth factor. In yet another embodiment, the one or more agents is selected from the group consisting of platelet-derived growth factor (PDGF), epidermal growth factor (EGF), fibroblast growth factor (FGF), basic fibroblast growth factor (bFGF), vascular endothelial growth factor (VEGF), keratinocyte growth factor (KGF), transforming growth factor alpha (TGFα), transforming growth factor beta (TGFβ), transforming growth factor beta-1 (TGFβ1), transforming growth factor beta-2 (TGFβ2), insulin-like growth factor (IGF), nerve growth factor (NGF), hepatocyte growth factor (HGF), insulin, hydrocortisone, urogastrone, platelet-derived wound healing factor (PDWHF), brain-derived neurotrophy factor (BDNF), platelet factor IV (PF IV), tumor necrosis factor (TNF), granulocyte colony stimulating factor (GCSF), colony-stimulating factors (CSF), bone morphogenetic protein (BMP), osteocalcin, osteopontin, interleukin-1, interleukin-6, interleukin-8 (IL-8), interleukin-11, and growth differentiation factor (GDF), or combinations thereof. In another embodiment, the one or more agents synthesized by and secreted from one or more cells cultured in the cell culture medium is present in the conditioned medium at a concentration selected from the group consisting of about at least 2 times, about 2 times, about 3 times, about 4 times, about 5 times, about 6 times, about 7 times, about 8 times, about 9 times, about 10 times, about 11 times, about 12 times, about 13 times, about 14 times, about 15 times, about 16 times, about 17 times, about 18 times, about 19 times, about 20 times, about 25 times, about 30 times, about 40 times, about 50 times, about 60 times, about 70 times, about 80 times, about 90 times, and about 100 times, increased as compared to the concentration in the cell culture medium before culturing. In still another embodiment, the cells are cultured in the cell culture medium for at least 24 hours, optionally for at least 48 hours or for at least 72 hours. In yet another embodiment, the biocompatible composition does not comprise cells. In another embodiment, the conditioned cell medium is concentrated, optionally wherein the conditioned cell medium is concentrated by tangential flow filtration. In still another embodiment, the polymer matrix is agarose, such as agarose derived from seaweed. In yet another embodiment, the agarose is low melting point agarose or ultra-low melting point agarose. In another embodiment, the agarose is selected from the group consisting of about 0.8% to 3.0% weight to volume (w:v), about 0.9% w:v, about 1.0% w:v, about 1.1% w:v, about 1.2% w:v, about 1.3% w:v, about 1.4% w:v, about 1.5% w:v, about 1.6% w:v, about 1.7% w:v, about 1.8% w:v, about 1.9% w:v, about 2.0% w:v, about 2.1% w:v, about 2.2% w:v, about 2.3% w:v, about 2.4% w:v, about 2.5% w:v, about 2.6% w:v, about 2.7% w:v, about 2.8% w:v, about 2.9% w:v, and about 3.0% w:v. In still another embodiment, the conditioned cell medium is about 50% of the volume of the biocompatible composition.

In another aspect, a method for producing a biocompatible composition, comprising (a) culturing cells in a cell culture medium; (b) separating the cultured cells from the cell culture medium conditioned with one or more agents synthesized by and secreted from the cells in the cell culture medium to produce a conditioned cell medium; and (c) mixing the conditioned cell medium with a biocompatible polymer matrix, is provided.

As described above, numerous embodiments are contemplated for any aspect of the present invention described herein. For example, in one embodiment, the cells are fibroblasts, such as dermal fibroblasts and especially neonatal dermal fibroblasts. In another embodiment, the cells are osteoblasts. In still another embodiment, the cells are fibroblasts and osteoblasts. In yet another embodiment, the cells are a co-culture of fibroblasts and osteoblasts. In another embodiment, the cells are actively proliferating cells. In still another embodiment, the cell culture medium comprises a basal cell culture medium and further comprises one or more supplements selected from the group consisting of fetal bovine serum (FBS), L-glutamine, human epidermal growth factor (EGF), basic fibroblast growth factor (bFGF), and ascorbic acid. In yet another embodiment, the basal cell culture medium is Dulbecco's modified eagle medium (DMEM). In another embodiment, the supplement is a recombinant growth factor, such as a human recombinant growth factor. In still another embodiment, the one or more agents comprises a growth factor. In yet another embodiment, the one or more agents is selected from the group consisting of platelet-derived growth factor (PDGF), epidermal growth factor (EGF), fibroblast growth factor (FGF), basic fibroblast growth factor (bFGF), vascular endothelial growth factor (VEGF), keratinocyte growth factor (KGF), transforming growth factor alpha (TGFα), transforming growth factor beta (TGFβ), transforming growth factor beta-1 (TGFβ1), transforming growth factor beta-2 (TGFβ2), insulin-like growth factor (IGF), nerve growth factor (NGF), hepatocyte growth factor (HGF), insulin, hydrocortisone, urogastrone, platelet-derived wound healing factor (PDWHF), brain-derived neurotrophy factor (BDNF), platelet factor IV (PF IV), tumor necrosis factor (TNF), granulocyte colony stimulating factor (GCSF), colony-stimulating factors (CSF), bone morphogenetic protein (BMP), osteocalcin, osteopontin, interleukin-1, interleukin-6, interleukin-8 (IL-8), interleukin-11, and growth differentiation factor (GDF), or combinations thereof. In another embodiment, the one or more agents synthesized by and secreted from one or more cells cultured in the cell culture medium is present in the conditioned medium at a concentration selected from the group consisting of about at least 2 times, about 3 times, about 4 times, about 5 times, about 6 times, about 7 times, about 8 times, about 9 times, about 10 times, about 11 times, about 12 times, about 13 times, about 14 times, about 15 times, about 16 times, about 17 times, about 18 times, about 19 times, about 20 times, about 25 times, about 30 times, about 40 times, about 50 times, about 60 times, about 70 times, about 80 times, about 90 times, and about 100 times, increased as compared to the concentration in the cell culture medium before culturing. In still another embodiment, the cells are cultured in the cell culture medium for at least 24 hours, optionally for at least 48 hours or for at least 72 hours. In yet another embodiment, the biocompatible composition does not comprise cells. In another embodiment, conditioned cell medium is concentrated before mixing the conditioned cell medium with a biocompatible polymer matrix, optionally wherein the conditioned cell medium is concentrated by tangential flow filtration. In still another embodiment, the polymer matrix is agarose, such as agarose derived from seaweed. In yet another embodiment, the agarose is low melting point agarose or ultra-low melting point agarose. In another embodiment, the agarose is selected from the group consisting of about 0.8% to 3.0% weight to volume (w:v), about 0.9% w:v, about 1.0% w:v, about 1.1% w:v, about 1.2% w:v, about 1.3% w:v, about 1.4% w:v, about 1.5% w:v, about 1.6% w:v, about 1.7% w:v, about 1.8% w:v, about 1.9% w:v, about 2.0% w:v, about 2.1% w:v, about 2.2% w:v, about 2.3% w:v, about 2.4% w:v, about 2.5% w:v, about 2.6% w:v, about 2.7% w:v, about 2.8% w:v, about 2.9% w:v, and about 3.0% w:v. In still another embodiment, the conditioned cell medium is about 50% of the volume of the biocompatible composition.

In still another aspect, a biocompatible composition of the present invention can be used in the preparation of a pharmaceutical preparation, optionally wherein the pharmaceutical preparation is a topically applied periodontal treatment.

In still another aspect, a method of growing bone or inhibiting bone resorption in a subject, the method comprising administering to a site in need of bone growth and/or bone resorption inhibition in the subject an effective amount of a biocompatible composition of the present invention, optionally wherein the method enhances total osseointegration, vertical osseointegration, and/or lateral osseointegration of new bone growth at the periodontal site, is provided. In one embodiment, the subject has a bone fracture, bone deficiency, metastatic bone disease, osteoarthritis, osteoporosis, and/or osteolytic bone disease.

In yet another aspect, a method of treating a periodontal condition in a subject, the method comprising administering to a periodontal site in need of a) gum and/or bone growth and/or b) gum erosion and/or bone resorption inhibition in the subject an effective amount of a biocompatible composition of the present invention, optionally wherein the method enhances total osseointegration, vertical osseointegration, and/or lateral osseointegration of new bone growth at the periodontal site, is provided.

As described above, numerous embodiments are contemplated for any aspect of the present invention described herein. For example, in one embodiment, the subject has periodontal disease, gum inflammation, tooth decay, gum disease, gingivitis, and/or periodontitis. In another embodiment, bone mass is maintained or increased, bone density is maintained or increased, gum tissue is maintained or increased, or any combination thereof. In still another embodiment, an effective amount of a therapeutic agent that a) promotes gum and/or bone growth and/or b) inhibits gum erosion and/or bone resorption is administered to a subject. In yet another embodiment, administering a biocompatible composition and administering a therapeutic agent is sequential or simultaneous. In another embodiment, a therapeutic agent is selected from the group consisting of bone morphogenetic factors, anti-resorptive agents, osteogenic factors, cartilage-derived morphogenetic proteins, growth hormones, estrogens, bisphosphonates, statins, differentiating factors, analgesics, anesthetics, antimicrobial agents, antibacterial agents, antiviral agents, antifungal agents, antibiotics, anti-inflammatory agents, antioxidants, antiseptic agents, immunostimulating agents, and combinations thereof. In still another embodiment, the biocompatible composition is topically administered to the site. In yet another embodiment, the topical administration is selected from the group consisting of a wound dressing, surgical closure, stapling, adhesive strip, bioadhesive, or gum flap. In another embodiment, the subject is a mammal, such as a human, a cat, a dog, a horse, or a rodent. In still another embodiment, the mammal is an animal model of a disorder in need of periodontal a) gum and/or bone growth and/or b) gum erosion and/or bone resorption inhibition.

These and other objects, advantages and features of the present invention will become apparent to those of ordinary skill in the art having read the following detailed description.

BRIEF DESCRIPTION OF FIGURES

FIG. 3A depicts a scratch assay using osteoblast unconditioned media. After 24 hrs of growth, osteoblasts grew to fill approximately 40% of the original gap. After 48 hrs of growth, osteoblasts grew to fill approximately 50% of the original gap with very little communication between the opposing sides. FIG. 3B depicts a scratch assay using osteoblast conditioned media. After 24 hrs of growth osteoblasts grew to fill approximately 40% of the original gap. After 48 hrs of growth, osteoblasts grew to fill approximately 75% of the original gap with osteoblasts communicating from opposite sides.

DETAILED DESCRIPTION OF THE INVENTION

Figure 1:
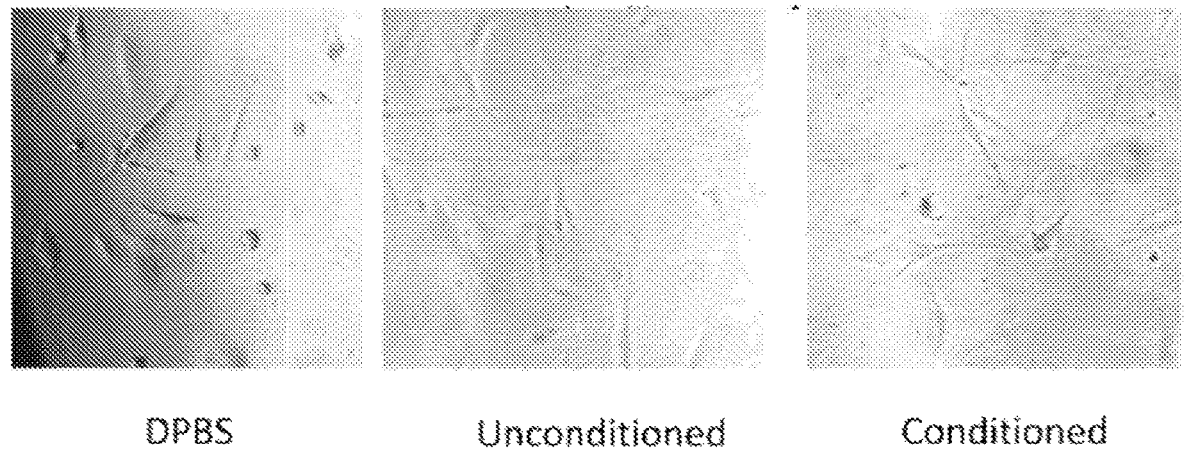
FIG. 1 depicts photomicrographs of cell morphology showing that there was no discernible effect on cell size or morphology between respective media.

The present invention provides biocompatible compositions comprising polymer matrix (e.g., agarose) infused with conditioned cell media comprising one or more cultured agents synthesized and secreted from one or more cultured cells (e.g., fibroblasts and/or osteoblasts). Said compositions can be used in methods for inducing or promoting gum growth and/or bone growth, as well as for reducing or preventing bone deterioration in a subject (e.g., human or animal). The methods generally comprise administering to the subject an effective amount of the biocompatible composition. The methods of the present invention, which are non-surgical, non-invasive and safe, can be used for the treatment and/or prevention of disease states or conditions associated with gum and/or bone degradation, gum and/or bone deterioration and/or gum and/or bone degeneration including, but not limited to, periodontal disease, osteoarthritis, metastatic bone disease, and osteolytic bone disease. Additional regenerative uses are contemplated, including but not limited to, stimulating wound healing, regenerating bone, gum, or tissue, and treating dental-related diseases, disorders, and conditions, such as periodontitis, gingivitis, and gum disease. Pharmaceutical compositions and kits comprising biocompatible compositions are also provided that can be used to perform the methods.

The biocompatible compositions provided herein offer physicians a therapeutic alternative/adjunct to shorten recovery times and improve overall patient results with respect to regenerative processes using conditioned cell media comprising a plethora of cultured agents, such as cytokines and growth factors. The heterogeneous composition of cultured agents, such as growth factors released from proliferating, cultured fibroblasts and osteoblasts, provide a complete source of cytokines and growth factors to stimulate fibroblast proliferation and differentiation involved in gum regeneration, and osteoblast proliferation/maturation involved in bone regeneration, respectively.

To date, there exists no product currently available on the market that comprises growth factors endogenously released from actively proliferating fibroblasts or osteoblasts. GEM21® (Osteohealth) is one product on the market that utilizes recombinant PDGF in order to encourage bone growth, but it is a synthetic calcium phosphate growth factor-enhanced matrix used as a dental bone filling device. Other products, such as Emdogain® (Straumann), which is a protein-containing gel comprising enamelin and ameloblastin, can promote ameloblast activity and enamel matrix protein to treat bone defects due to periodontal disease.

These existing products fail to recognize that regenerative processes, such as periodontal regeneration and bone regeneration, are complex biological processes. These biological processes involve several growth factors, which are lacking in the existing products, resulting in less than optimal results.

By contrast, the present invention provides a biocompatible composition comprised of a complete mixture of growth factors endogenously released by cultured cells, such as fibroblasts and osteoblasts. The rationale behind this is to address the complexity of regenerative processes, such as gum and bone regeneration, and also to be able to achieve this using one modality. Without being bound by theory, the use of a polymer matrix (e.g., agarose) serves as a reservoir for the sustained release of growth factors allowing increased exposure to the area of trauma or bone loss, ultimately resulting in increased cell proliferation.

I. DEFINITIONS

The articles "a" and "an" are used herein to refer to one or to more than one (i.e., to at least one) of the grammatical object of the article. By way of example, "an element" means one element or more than one element.

The term "about" generally refers to a value that is within 10% of a recited or any range in between, inclusive, such as a range value that is within 5% less and 8% more than the stated range, unless otherwise specified.

The term "bone condition" includes any condition where it is desirable to increase, improve or promote bone mass and/or bone density and/or prevent, inhibit or reduce the loss of bone mass and/or bone density. The term "bone condition" encompasses any condition that increases osteoclast and/or osteoblast number, increases osteoclast and/or osteoblast activity, increases bone resorption, increases marrow fibrosis, or alters the calcium content of bone.

The term "bone loss" refers to any situation in which skeletal mass, substance or matrix or any component of the skeleton, such as calcium and phosphate, is decreased or the bone or the tooth is lost, damaged, or weakened such as in terms of its ability to resist being broken. The term "bone loss" also encompasses any situation characterized by bone deterioration, bone degradation, bone degeneration, loss of bone mass, loss of bone density, and any combinations of these conditions.

The term "effective amount" refers to any amount of a molecule, agent, factor and/or biocompatible composition provided herein that is sufficient to fulfill its intended purpose(s) (e.g., the purpose can be to treat or prevent bone loss, for example, bone loss associated with periodontal disease).

The terms "local" and "topical", refer to the delivery, administration or application of a compound or composition, is meant to specify that the compound or composition is delivered, administered or applied directly to the site of interest (e.g., in the oral cavity for an oral disorder such as a periodontal disease) for a localized effect. In certain embodiments, local or topical administration is effected without any significant absorption of components of the composition into the subject's blood stream.

The term "osteoblast" refers to a cell that secretes the matrix for bone formation. The term "osteoclast" refers to a large multinucleate bone cell that absorbs bone tissue during growth and healing.

The term "osteoconductive" refers to the ability of a compound, composition, process or material to provide an environment for ingrowth and orientation of osteogenic cells from surrounding tissues.

The term "osteogenic" refers to the ability of a compound, composition, process or material to cause (e.g., initiate, promote, facilitate, accelerate, enhance, stimulate, and the like) bone formation.

The term "osteoinductive" refers to the ability of a compound, composition, process or material to induce the production of osteoblasts from precursor cells, in particular mesenchymal stem cells. The osteoinductive compound, composition, process or material can act directly (e.g., such as a growth factor which interacts with precursor cells to induce the osteoblast differentiation) or it can act indirectly by inducing the production of osteoinductive growth factors.

The terms "oral disorder" is used interchangeably with "dental disorder" and includes a disorder, disease or condition which is caused or characterized by an abnormally low or insufficient level of oral bone (e.g., bone in the oral cavity). Exemplary oral bone includes alveolar bone and basal bone. Oral disorders that can be treated according to the invention, by increasing bone mass or bone growth include, but are not limited to, periodontal disease, alveolar bone loss, gingivitis, osteoporosis, osteopenia, oral bone resection, oral bone fracture, arthritis, osteoarthritis, osteotomy bone loss, childhood idiopathic bone loss, and the like. Destructive oral bone disorders that can be treated according to the invention include, but are not limited to, osteoporosis, osteopenia, osteoarthritis and osteolytic lesions such as those caused by neoplastic disease, radiotherapy, or chemotherapy. Also contemplated by the present invention is the regeneration of other oral tissues including soft tissues, epithelium, and connective tissues, such as collagen and blood vessels.

The term "periodontal diseases" include all diseases of the periodontal tissues that surround and support the teeth (see, for example, D. M. Williams et al., *Pathology of Periodontal Disease* (1992) Oxford University Press). These include the gingiva, cementum, periodontal ligament, alveolar process bone, and dental supporting bone. Specifically, periodontal diseases include gingivitis and periodontitis. Gingivitis is a disease in which inflammation is localized within the gingiva and no lesion occurs in the bone between the teeth and gingiva. Periodontitis is a disease in which gingival inflammation reaches the periodontal ligament and alveolar bone. Left untreated, periodontitis can lead to tooth loss. Periodontal diseases also encompass a larger set of inflammatory diseases affecting the periodontium. For example, such disease include dental plaque-induced gingival diseases; chronic (previously adult) periodontitis; aggressive periodontitis (formerly early-onset, prepubertal, juvenile or rapidly progressive periodontitis); necrotising periodontal diseases; abcesses of the periodontium; and post-operative bacterial infections (in particular those which are caused, transmitted and/or exacerbated by *P. gingivalis*).

The term "subject" refers to any healthy animal, mammal or human, or any animal, mammal or human afflicted with a condition of interest (e.g., periodontal disease). The term "subject" is interchangeable with "patient" or "individual." They refer to a higher vertebrate, preferably a human or another mammal (e.g., a mouse, rat, rabbit, monkey, dog, cat, pig, cow, horse, and the like) that can suffer from a disease state or condition for which administration of the biocompatible compositions of the present invention is beneficial but may or may not have the disease state or condition. In many embodiments, the subject is suffering from or is susceptible to (i.e., exhibits a high or higher risk of developing) a bone condition, for example, a bone condition associated with bone loss. In certain embodiments, the subject is a human being. The terms do not denote a particular age, and thus encompass adults, children and newborns. In other embodiments, the subject is an animal model of a disorder of interest, such as bone loss and/or periodontal disease.

The term "suture" refers to a stitch or row of stitches holding together the edges of a wound or surgical incision together in order to achieve tissue repair. Healing by suturing consists of bringing the edges of the wound together by introducing a suture in the tissues using a metal needle joined at one of its ends, passing the needle successively between both sides of the incision, thereby passively facilitating the closure of the wound. Sutures are also used in surgical practice to stop bleeding (haemostasis) and to repair organs and other structures of the human body. In some situations; these sutures are particularly delicate due to the healing difficulties of the tissues they are used on. This is the case of sutures used for the colon wall, for tendons and in microsurgery involving nerve tissue and blood vessels.

The term "treatment" is used herein to characterize a process/method that is aimed at (1) delaying or preventing the onset of a disease state or condition; (2) slowing down or stopping the progression, aggravation or deterioration of the symptoms of a clinical condition, (3) bringing about ameliorations of the symptoms of the condition; and/or (4) curing the condition. The treatment can be administered before the onset of the condition for a prophylactic action or it can be administered after initiation of the condition for a therapeutic action.

The term "wound" used herein refers to a wound such as abrasion, burn, chap, detrition, cut, diabetic lower leg ulcer, laceration, deep cut, organ transplant, bullet wound, incision, lower leg ulcer, decubital ulcer, burn scar, scratch, burnt skin, sore skin, decubital scar, stab wound, transplant, venous ulcer or a wound associated with surgery or plastic surgery.

II. BIOCOMPATIBLE COMPOSITIONS AND METHODS OF MAKING BIOCOMPATIBLE COMPOSITIONS

Provided herein are biocompatible compositions comprised of polymer matrix (e.g., agarose) infused with conditioned cell media from cultured cells (e.g., both fibroblasts and osteoblasts). For example, the ratio of conditioned cell media from fibroblasts as compared to osteoblasts can be 5%:95%, 10%:90%, 15%:85%, 20%:80%, 25%:75%, 30%:70%, 35%:65%, 40%:60%, 45%:55%, 50%:50%, 55%:45%, 60%:40%, 65%:35%, 70%:30%, 75%:25%, 80%:20%, 85%:15%, 90%:10%, 95%:5%, or more, or any range in between, inclusive, such as 40%:60% to 60%:40%, The conditioned cell media, containing cultured agents, represent a heterogeneous composition of growth factors released during cell proliferation intended to stimulate regenerative process that include the inflammatory, proliferative, and maturation stages. Together, the growth factors secreted into the conditioned media from actively proliferating cells (e.g., fibroblasts and osteoblasts) represent a complete mixture of growth factors and proteins necessary both for regenerative uses, such as periodontal, bone, and skin regeneration and reconstruction. The use of polymer matrix (e.g., agarose) serves as a reservoir for the sustained release of growth factors allowing increased exposure to the area of trauma, ultimately resulting in increased cell proliferation.

The present invention also provides a method for producing a composition or a preparation containing a conditioned cell medium containing one or more cultured agents produced by cultured cells. The method includes culturing cells, for example fibroblasts and/or osteoblasts, in order for the cells to synthesize and secrete one or more cytokines, growth factor, and/or proteins into the medium. The resulting conditioned cell medium, now containing one or more cultured agents, is separated from the cultured cells and combined with a polymer matrix to form a biocompatible composition.

A. Conditioned Cell Media

The term "conditioned cell medium" or "conditioned medium" refers to cell culture medium that has been used by the cells of a cell culture as a source of nutrients, vitamins, hormones, and inorganic compounds and salts and by having contacted the cell culture, now have added cell products, or "cultured agents," such as cytokines, proteins, extracellular matrix components, or any combination thereof, synthesized and secreted by the cells into the medium. Conditioning is the act of the cells' synthesis and secretion of cytokines, proteins and extracellular matrix components, into fresh medium upon contact, exposure, exchange and interaction with between the cells and the medium for a time, preferably a time between 6 hours to 3 days, more preferably 12 hours to 2 days, to condition the medium, such as at least about 6 hours, at least about 8 hours, at least about 10 hours, at least about 12 hours, at least about 14 hours, at least about 16 hours, at least about 12 hours, at least about 14 hours, at least about 16 hours, at least about 18 hours, at least about 20 hours, at least about 22 hours, at least about 24 hours, at least about 30 hours, at least about 36 hours, at least about 42 hours, at least about 48 hours, at least about 54 hours, at least about 60 hours, at least about 66 hours, at least about 72 hours, at least about 3 days, at least about 4 days, at least about 5 days, at least about 6 days, at least about 7 days, at least about 2 weeks, inclusive, or any range in between such as between 24 hours and 3 days. The conditioned cell medium is removed from the culture apparatus containing the cultured cells and is collected for purification of its cultured agents, or is used whole or in part as a pharmaceutical, cosmetic, or wound healing composition for use in a variety of regenerative processes described herein, or for use in in vitro cell culture.

Cytokines are proteins that exert changes in the function or activity of a cell such as differentiation, proliferation, secretion, or motility. Growth factors are a subset of cytokines that are also proteins that cause changes in functions or activities that promote or inhibit cellular growth, proliferation, migration, or other related cellular events. Chemokines are another subset of cytokines that attract and guide T-cells, B-cells, and other chemokine-responsive cells to specific tissues in the body. Lymphokines are still another subset of cytokines involved in immune response. As used herein, the term "cytokines," includes cytokines, including growth factors, chemokines and lymphokines, and are not limited to their normal structure and function, but can also include their naturally occurring variants and hybrids. The cultured agents of the invention can comprise cytokines, growth factors, and proteins.

Throughout their fabrication and when fully formed, cultured cells contain living cells that synthesize and secrete an array of cytokines and other substances into the medium bathing the cultured cells. The cultured cells typically consist of fibroblasts and osteoblasts cells, but can comprise any variety of cells. In the process of fabricating and culturing cells, the fibroblasts and osteoblasts can provide a tissue-like environment, an organized co-culture incorporating an extracellular matrix, for cell-cell and cell-matrix interactions similar to those that occur in native tissue and/or bone (e.g., periodontal tissue and bone). These interactions in the developing cell culture allow for a wide profile of cytokine expression and secretion to the media to induce other cells in the culture to perform functions of extracellular matrix development, basement membrane production, and cell proliferation and differentiation.

The conditioned media can comprise growth factors that include the well-known platelet-derived growth factor (PDGF), which is important for cell growth, cell division, and angiogenesis. Recombinant PDGF is currently FDA-approved for bone repair and regeneration. Other growth factors include, but not limited to, epidermal growth factor (EGF), fibroblast growth factor (FGF), basic fibroblast growth factor (bFGF), and vascular endothelial growth factor (VEGF), all of which contribute to the proliferative phase (growth of new tissue) that involves angiogenesis, collagen deposition, granulation tissue formation, and epithelialization. Conditioned media from proliferating osteoblasts comprise growth factors similarly released from proliferating fibroblasts such as described above, and the unique proteins osteocalcin and osteopontin, which compose the organic matrix of bone. Other cytokines and growth factors that are produced by cultured cells include, but are not limited to, keratinocyte growth factor (KGF), transforming growth factor alpha (TGFα), transforming growth factor beta (TGFβ), including transforming growth factor beta-1 (TGFβ1) and transforming growth factor beta-2 (TGFβ2), insulin-like growth factor (IGF), nerve growth factor (NGF), and hepatocyte growth factor (HGF). Additional, components can include biologically active agents such as insulin, hydrocortisone, urogastrone, platelet-derived wound healing factor (PDWHF), brain-derived neurotrophic factor (BDNF), platelet factor IV (PF IV), tumor necrosis factor (TNF), granulocyte colony stimulating factor (GCSF), colony-stimulating factors (CSF), bone morphogenetic protein (BMP), and growth differentiation factor (GDF). It should be noted that the aforementioned terms in parentheticals are abbreviations commonly known and used in the art for the formal nomenclature preceding them.

A number of interleukins, including interleukin-1 (IL-1), interleukin-6 (IL-6), interleukin-8 (IL-8), interleukin-11 (IL-11), can also synthesized by the cultured cells and are also a feature of this invention. In the chemokine subset, interleukins affect cell apoptosis. It should be noted that the aforementioned terms in parentheticals are abbreviations commonly known and used in the art for the formal nomenclature preceding them.

Other cytokines and growth factors that comprise the cultured agents of the invention include, but not limited to, amphiregulin, angiogenin, angiopoietin-2, DTK, EGF-R, ENA-78, FAS, FGF-I, FGF-2, FGF-6, FGF-7, FGF-9, FIT-3 ligand, GCP-2, GM-CSF, GRO-alpha, HGF, IGF-I, IGF-2, IGFBP-2, IL-lalpha, IL-lbeta, L-IRA, IL-6R, Leptin, MCP-I, MCP-2, M-CSF, osteoprotegrin, PIGF, RANTES, stem cell factor, TGFbeta3, TIMP-I, TIMP-2, TRAIL, and UPAR.

The conditioned cell media of the present invention can be produced by cultured cells, including but not limited to, osteoblasts, fibroblasts, keratinocytes, dermal fibroblasts, epidermal cells, osteoclasts, epithelial cells, endothelial cells, adipocytes, myocytes, chondrocytes, osteocytes, neurons, astrocytes, oligodentrocytes, multipotent stem cells, undifferentiated stem cells, pluripotent stem cells, adult stem cells, hepatocytes and pancreatic cells, or any combinations thereof. In certain embodiments, the cells are cultured together as a co-culture of both osteoblasts and fibroblasts.

Additional cell types for use in this invention can be derived from mesenchyme. In certain embodiments, the preferred cell types are osteoblasts, fibroblasts, stromal cells, and other supporting connective tissue cells, or, as in the most preferred embodiment, human osteoblasts and fibroblasts. Human fibroblast cell strains can be derived from a number of sources, including, but not limited to neonate male foreskin, dermis, tendon, lung, umbilical cords, cartilage, urethra, corneal stroma, oral mucosa, and intestine. The human cells can include, but need not be limited to, fibroblasts, smooth muscle cells, chondrocytes and other connective tissue cells of mesenchymal origin. In certain embodiments, the origin of the matrix-producing cell used in the production of a tissue construct can be derived from a tissue type that it is to resemble or mimic after employing the culturing methods of the invention. For instance, a multilayer sheet construct is cultured with fibroblasts to form a living connective tissue construct; or myoblasts, for a skeletal muscle construct. More than one cell type can be used to fabricate a tissue construct. Cell donors can vary in development and age. Cells can be derived from donor tissues of embryos, neonates, or older individuals including adults. Embryonic progenitor cells, such as mesenchymal stem cells, can be used in the invention and induced to differentiate to develop into the desired tissue.

Although human cells are preferred for use in the invention, the cells to be used in the method of are not limited to cells from human sources. Cells from other mammalian species including, but not limited to, equine, canine, porcine, bovine, feline, caprine, and ovine sources can be used. Murine cells, and other cells from rodent sources, can also be used. In addition, genetically engineered cells that are spontaneously, chemically or virally-transfected can also be used in the present invention. For those embodiments that incorporate more than one cell type, mixtures of normal and genetically modified or transfected cells can be used and mixtures of cells of two or more species or tissue sources can be used, or both.

Recombinant or genetically-engineered cells can be used in the production of the tissue construct to create a tissue construct that acts as a drug delivery graft for a patient needing increased levels of natural cell products or treatment with a therapeutic. The cells can produce recombinant cell products, growth factors, hormones, peptides or proteins for a continuous amount of time or as needed when biologically, chemically, or thermally signaled due to the conditions present in culture. Cells can also be genetically engineered to express cytokines, growth factors, proteins or different types of extracellular matrix components which are either 'normal' but expressed at high levels or modified in some way to make a cell products that are therapeutically advantageous for regenerative uses, including improved wound healing, facilitated or directed neovascularization. These procedures are generally known in the art, and are described in Sambrook et al, Molecular Cloning, A Laboratory Manual, Cold Spring Harbor Press, Cold Spring Harbor, N.Y. (1989), incorporated herein by reference. All of the above-mentioned types of cells can be used according to the present invention for the production of cultured cells that will synthesize the conditioned media containing agents, such as cytokines and/or growth factors. In some embodiments, cells in a cultured cell are cultured in a scaffold that supports the cells in an arrangement and composition that mimics that found in normal bone, skin, or tissue of interest.

The number of cells, concentration of cell culture media, and the cell culture substrate volume can be regulated according to well-known methods in the art in order to optimize the proliferation of the cells. The cultures can also be maintained in an incubator to ensure sufficient environmental conditions of controlled temperature, humidity, and gas mixture for the culture of cells. Preferred conditions are between about 34° C. to about 38° C., more preferably 37±1° C. with an atmosphere between about 5-10+1% $CO_2$ and a relative humidity (Rh) between about 80-90%.

The cultured cells are nourished by contacting a culture medium that becomes conditioned by the cells as they metabolize components from the medium and secrete cytokines, growth factors and other proteins into it. A defined medium means a culture medium for use in cell culture that contains chemically defined components and is free of undefined animal organ or tissue extracts, for example, serum, pituitary extract, hypothalamic extract, placental extract, or embryonic extract or proteins and factors secreted by feeder cells. In some embodiments, the cell culture media can be free of undefined components and defined biological components derived from non-human sources. Although the addition of undefined components is not preferred, they can be used in accordance with the disclosed methods at any point in culture in order to generate the conditioned media. When the invention is carried out utilizing screened human cells cultured using chemically defined components derived from no non-human derived biological components, the resultant tissue construct is a defined human bone, tissue, or skin construct. The advantages in using such a construct to produce the conditioned medium of the invention is the elimination of the concern that adventitious animal or cross-species virus contamination and infection can be present in the tissue construct or the conditioned medium.

Culture medium, when fresh and unused, is comprised of a nutrient base that can also be further supplemented with other components. The skilled artisan can determine appropriate nutrient bases in the art of mammalian cell culture. For example, many commercially available nutrient sources are useful on the practice of the present invention. These include commercially available nutrient sources which supply inorganic salts, an energy source, amino acids, and B-vitamins such as Dulbecco's Modified Eagle's Medium (DMEM); Minimal Essential Medium (MEM); M 199; RPMI 1640; Iscove's Modified Dulbecco's Medium (ED-MEM). Minimal Essential Medium (MEM) and M199 require additional supplementation with phospholipid precursors and non-essential amino acids. Commercially available vitamin-rich mixtures that supply additional amino acids, nucleic acids, enzyme cofactors, phospholipid precursors, and inorganic salts include Ham's F-12, Ham's F-10, NCTC 109, and NCTC 135. Albeit in varying concentrations, all basal media provide a basic nutrient source for cells in the form of glucose, amino acids, vitamins, and inorganic ions, together with other basic media components.

The base medium can be supplemented with components such as amino acids, growth factors, and hormones. Defined culture media for the culture of cells of the invention are described in U.S. Pat. No. 5,712,163 to Parenteau and in International PCT Publication No. WO95/31473, the disclosures of which are incorporated herein by reference. Other media are known in the art such as those disclosed in Ham and McKeehan, *Methods in Enzymology* (1979) 58:44-93, or for other appropriate chemically defined media, in Bottenstein et al. *Methods in Enzymology* (1979) 58:94-109. Common representative supplements are described below.

For example, insulin is a polypeptide hormone that promotes the uptake of glucose and amino acids to provide long term benefits over multiple passages. Supplementation of insulin or insulin-like growth factor (IGF) is necessary for long term culture as there will be eventual depletion of the cells' ability to uptake glucose and amino acids and possible degradation of the cell phenotype. Insulin supplementation is advisable for serial cultivation and can be provided to the media at a concentration range of preferably between about 0.5 µg/ml to about 50 µg/ml, more preferably at about 5 µg/ml. Appropriate concentrations for the supplementation of insulin-like growth factor, such as IGF-I or IGF-2, can be easily determined by one of skill in the art for the cell types chosen for culture.

Transferrin is in the medium for iron transport regulation. Iron is an essential trace element found in serum. As iron can be toxic to cells in its free form, in serum it can be supplied to cells bound to transferrin at a concentration range of preferably between about 0.05 to about 50 µg/ml, more preferably at about 5 µg/ml.

Triiodothyronine (T3) is a basic component and is the active form of thyroid hormone that is included in the medium to maintain rates of cell metabolism. Triiodothyronine can be supplemented to the medium at a concentration range between about 0 to about 400 pM, more preferably between about 2 to about 200 pM and most preferably at about 20 pM.

Either or both ethanolamine and o-phosphoryl-ethanol amine, which are phospholipids, can be added as a precursor in the inositol pathway and fatty acid metabolism. Supplementation of lipids that are normally found in serum is necessary in a serum-free medium. Ethanolamine and o-phosphoryl-ethanolamine can be provided to media at a concentration range between about $10^{-6}$ to about $10^{-2}$ M, more preferably at about $1\times10^{-4}$ M.

Selenium can be added to serum-free media to resupplement the trace elements of selenium normally provided by serum. Selenium can be provided at a concentration range of about $10^{-9}$ M to about $10^{-7}$ M, most preferably at about $5.3 \times 10^{-8}$ M.

The amino acid L-glutamine is present in some nutrient bases and can be added in cases where there is none or insufficient amounts present. L-glutamine can also be provided in stable form such as that sold under the mark, GlutaMAX-1™ (Gibco BRL, Grand Island, N.Y.). GlutaMAX-1™ is the stable dipeptide form of L-alanyl-L-glutamine and can be used interchangeably with L-glutamine and is provided in equimolar concentrations as a substitute to L-glutamine. The dipeptide provides stability to L-glutamine from degradation over time in storage and during incubation that can lead to uncertainty in the effective concentration of L-glutamine in medium. Typically, the base medium is supplemented with preferably between about 1 mM to about 6 mM, more preferably between about 2 mM to about 5 mM, and most preferably 4 mM L-glutamine or GlutaMAX-1™.

Growth factors, such as epidermal growth factor (EGF) and other growth factors described herein like bFGF, can also be added to the medium to aid in the establishment of the cultures through cell scale-up and seeding. For example, EGF in native form or recombinant form can be used. Human forms, native or recombinant, of EGF are preferred for use in the medium when fabricating a skin equivalent containing no non-human biological components. EGF and/or other growth factors can be provided at a concentration between about 1 to about 15 ng/mL, more preferably between about 5 to about 10 ng/mL.

The cell culture medium is typically prepared as set forth below in the examples. However, it should be understood that the components of the present invention can be prepared and assembled using conventional methodology compatible with their physical properties. It is well-known in the art to substitute certain components with an appropriate analogue or functionally equivalent acting agent for the purposes of availability or economy and arrive at a similar result. Naturally occurring growth factors can be substituted with recombinant or synthetic growth factors that have similar qualities and results when used in the performance of the invention.

Cell culture media in accordance with the present invention are sterile. Sterile components are bought or rendered sterile by conventional procedures, such as filtration, after preparation. Proper aseptic procedures were used throughout the following Examples. For example, DMEM is obtained and other components are then added to complete the medium. Stock solutions of all components can be stored at $-20°$ C., with the exception of nutrient source that can be stored at $4°$ C. All solutions can be prepared as concentrated stocks.

The mode of supplying fresh medium to cultures is done by pipetting, decanting, or pumping the medium into the culture apparatus. Conditioning of the medium occurs by contacting the medium with cultured cells for a sufficient amount of time, usually for about 6 hours to 3 days or more to allow for the cells to absorb or take up nutrients and the like from the fresh medium and secrete cytokines, growth factors, and/or proteins into the medium. Since the cultured cells are in a constant metabolic state, only a short amount of time is needed to condition the medium. It is preferred that the construct and the medium contact each other for the exchange until the nutrients are nearly depleted from the fresh medium.

Conditioned medium is removed and collected from the cultures by pipetting, aspirating, decanting, draining, siphoning, or pumping at the time of each exchange of the conditioned medium with fresh medium. The conditioned media collections can be used individually as individual collections, or pooled together. The development of a cultured bone, tissue, or skin construct is marked with a number of events that produce a conditioned medium having a varying conditioned profile at each collection point. As separate collections, the conditioned medium will have certain secreted factors that can be desirable for a particular treatment indication or product. When combined by pooling the collections together, the conditioned medium will have a broader range of secreted factors for treatments or products.

Once collected, the conditioned medium is used as is collected or further processing is performed on the medium for purification or ease in application or storage before use. The conditioned medium can be lyophilized or evaporated to remove the liquid, or water, portion of the composition. Removal of water leaves a crystalline powder form of the conditioned medium containing the cultured agents: growth factors, cytokines, proteins and extracellular matrix components, with decreased volume. This form makes it easier to prepare products containing higher dosages of the cultured agents without diluting the preparation and thus making it easier to store because of its decreased volume.

The conditioned medium can also be concentrated using a filtration method, particularly one with a molecular weight cut-off or a series of molecular weight filters. The use of molecular weight filters will remove large components found in medium such as albumin, certain large molecular weight components found in serum, cells and cell debris. Although not required, it can be desirable to pre-filter the conditioned medium to remove these larger components prior to filtration with a smaller pore filter to prevent clogging and diminished filtration capacity of any subsequently employed filter. Other filtration and dialysis methods can be used to remove salt from the cell product composition. For example, tangential flow filtration can be employed to increase the concentration of cultured agents in the conditioned medium. In addition, tangential flow filtration can be employed to reduce the salt concentration in the conditioned medium. To reduce the concentration of the salt, as the aqueous component of the conditioned medium is removed, it is replaced with water. Indeed, the concentration of the cultured agents and reduction of the salt concentration can be repeated at least once so that the cultured agents are effectively rinsed of salts. The cultured agents can be further purified, fragmented, or conjugated to form a pure cytokine, protein, or extracellular matrix compositions or enhanced for directed delivery to a particular tissue, tissue structure or cell type. The purified and reduced salt aspects of the cultured agents make them more compatible, and are therefore preferred, for formulating topical preparations of the present invention.

The conditioned medium containing secreted agents, such as cytokines and/or growth factors, produced by cultured cells alone can be useful in cell culture or combined with a polymer matrix as described further herein. The conditioned medium can be used to grow and sustain cell lines by increasing cell proliferation and generation of vital new bone and/or gum tissue, control the proliferation and differentiation of stem and progenitor cells, and mesenchymal differentiation (such as differentiation of mesenchymal cells to bone cells). The conditioned medium is also used for making other tissue constructs for inhibiting or stimulating cell growth in particular layers or directions. The effect of the conditioned medium is believed to be concentrationdependent with higher concentrations producing a greater effect than lower concentrations.

B. Polymer Matrix

As indicated above, the biocompatible compositions of the present invention can comprise polymer matrix infused with conditioned cell media from cultured cells. In certain embodiments, the polymer matrix can be biodegradable. In certain embodiments, the polymer matrix can comprise polysaccharides. A variety of polysaccharides can be suitable as aqueous phase thickening agents. Examples of such polysaccharides include naturally-derived materials such as agar, agarose, alicaligenes polysaccharides, algin, alginic acid, acacia gum, amylopectin, chitin, dextran, cassia gum, cellulose gum, gelatin, gellan gum, hyaluronic acid, hydroxyethyl cellulose, methyl cellulose, ethyl cellulose, pectin, sclerotium gum, xanthan gum, pectin, trehelose, gelatin, and so on. In certain embodiments, the agarose can comprise a polysaccharide polymer matrix extracted from seaweed or biotanical extracts. The extracts can be provided in the biocompatible compositions, ranging from about 0.0001 to 10%, preferably about 0.0005 to 8%, and more preferably about 0.001 to 5% by weight of the total composition. Suitable botanical extracts include extracts from plants (herbs, roots, flowers, fruits, seeds) such as flowers, fruits, vegetables, and so on, including yeast ferment extract, *Padica pavonica* extract, *Thermus thermophilis* ferment extract, *Camelina sativa* seed oil, *Boswellia serrata* extract, olive extract, *Aribodopsis thaliana* extract, *Acacia dealbata* extract, *Acer saccharinum* (sugar maple), *Acidopholus*, acorns, aesculus, agaricus, agave, agrimonia, algae, aloe, citrus, brassica, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza glabra, Salix nigra, Macrocycstis pyrifera, Pyrus malus, Saxifraga sarmentosa, Vilis vinifera, Morus nigra, Scutellaria baicalensis, Anthemis nobilis, Salvia selarea, Rosmarinus officianalis, Citrus medica limonum, Panax ginseng*, and mixtures thereof.

In certain embodiments, the biocompatible compositions are formulated to provide a local controlled release of one or more of the active components. Any pharmaceutically acceptable carrier vehicle or formulation suitable for local administration can be employed. Slow release formulations known in the art include, without limitation, coated-pellets, polymer formulations (such as vesicles or liposomes), and microparticles (e.g., microspheres or microcapsules).

A wide variety of biodegradable materials can be used to provide controlled release. The controlled release material should be biocompatible and be degraded, dissolved or absorbed in situ in a safe and pharmaceutically acceptable manner so that the material is removed from the site of administration by natural tissue processes and in a suitable amount of time (e.g., less than one year, less than 6 months, and less than one month, less than one week, less than one day or less than a few hours). The controlled release carrier should not cause any unwanted local tissue reaction, nor should it induce systemic or local toxicity.

Suitable controlled release biodegradable polymers for use in the biocompatible compositions of the invention can comprise polylactides, polyglycolides, poly(lactide-co-glycolides), polyanhydrides, polyorthoesters, polycaprolactones, poly-saccharides, poly-phosphazenes, proteinaceous polymers and their soluble derivatives (such as gelation biodegradable synthetic polypeptides, alkylated collagen, and alkylated elastin), soluble derivatives of polysaccharides, polypeptides, polyesters, and polyorthoesters.

In certain embodiments, extracellular matrix proteins can be used to generate biocompatible scaffolds. For example, collagen is a common composition for use as a biodegradable scaffold. While collagen is the most preferred extracellular matrix composition for use in biocompatible compositions, other extracellular matrices can also be used, such as other collagens, both fibrillar and non-fibrillar collagen from the collagen family such as collagen types II, III, IV, V, VI5 VII, VIII5 IX, X5 XI, XII5 XIII, XTV, XV, XVI, XVII, XVIII, XIX5 other matrix proteins that can include, but are not limited to elastin, proteoglycans such as decorin or biglycan, or glycoproteins such as tenascin, vitronectin, fibronectin, laminin, thrombospondin I, and glycosaminoglycans (GAG) such as hyaluronic acid (HA). The dermal matrix can vary in composition and structure. Collagen sponges, biocompatible, bioremodelable, decellularized dermis, or collagen gels. Rather than provide extracellular matrix components to the dermal cells, they can be cultured on biodegradable mesh members (such as nylon or polygalactin (PGA)) to provide a culture support and cultured to produce extracellular matrix until the cells and their matrix envelope the support. In certain embodiments, collagen gels, such as those described in U.S. Pat. No. 4,485,096 to Bell, incorporated herein by reference, can be used. Contracted collagen gels can be disposed on a bulk acellular collagen layer on a porous membrane to anchor the gel to the membrane and to prevent excessive radial contraction of the gel. Methods for incorporating a bulk acellular collagen layer are described in U.S. Pat. No. 5,536,656 to Kemp, et al., in Wilkins, L. M., et al. *Biotechnology and Bioengineering* (1994) 43:747-756, and in Parenteau, N. L. Skin equivalents. In: T. Leigh and F. Watt (eds.), The Keratinocyte Handbook Cambridge University Press, London (1994), the disclosures of which are incorporated herein by reference. Tissue equivalent and the acellular, hydrated collagen gel can be prepared using collagen derived from skin and tendon, including rat tail tendon, calfskin collagen, and calf extensor tendon. Other sources of collagen would be suitable. A collagen composition derived from calf common digital extensor tendon and methods of deriving such collagen compositions are disclosed in U.S. Pat. No. 5,106,949 to Kemp, the disclosure of which is incorporated herein by reference.

In certain embodiments, the polymer matrix can comprise agarose or agarose-like material. Agarose offers several advantages. First, it is all-natural and generally derived from seaweed. Consisting of a relatively simple repeating disaccharide, agarose offers chemical and thermal stability, allowing it to maintain a gel-like consistency at room temperature serving as a physical reservoir for growth factors and proteins, while minimizing any interactions with the aforementioned in terms of binding or altering their structure, thus preserving their biologic activity. This allows both the immediate and sustained passive secretion of growth factors and proteins involved in the biologic process of periodontal regeneration and bone growth. Over time, the matrix will dissolve and undergo resorption.

Secondly, when transitioning from the aqueous phase to a semi-solid gelatinous phase the agarose forms a three-dimensional mesh network forming a network of channels allowing the pre-infused growth factors and cytokines to passively diffuse out of the agarose to stimulate cell proliferation and also allowing cells to exert their paracrine-like effect by allowing passage of byproducts of metabolism to traverse one side of the matrix to the other enhancing the repair and growth.

In certain embodiments, a low-melting point agarose is preferred matrix due to its chemical and thermal stability and its inertness with respect to interaction (binding or alteration) of proteins. When cooled to a gelatinous state, the agarose gel represents a physical reservoir for the respective growth factors resulting in both an immediate and continuous release of growth factors related to periodontal and bone regeneration. In addition, the agarose polymer chains form a three-dimensional mesh network of channels allowing passive diffusion of growth factors and other naturally occurring cytokines augmenting the paracrine-like effect of cell-to-cell interactions required for proliferation and differentiation at a cellular level resulting in the phenotypic changes represented as periodontal growth and new bone morphogenesis.

In certain embodiments, the agarose can be a low melting agarose or even an ultra-low melting agarose (SeaPrep™ Agarose from Lonza). The term "low melting point agarose" generally refers to agarose that will melt into a fluid at a temperature of around 65° C. or higher (see, for example, UltraPure™ low melting point agarose, ThermoFisher Scientific). The term "ultra-low melting point agarose" generally refers to agarose that will melt into a fluid at a temperature of around 40-50° C. or higher (see, for example, Agarose A5030, Sigma-Aldrich, and SeaPrep® Agarose, Lonza). Such agarose compositions can be at concentration of 0.8% weight to volume (w:v), about 0.9% w:v, about 1.0% w:v, about 1.1% w:v, about 1.2% w:v, about 1.3% w:v, about 1.4% w:v, about 1.5% w:v, about 1.6% w:v, about 1.7% w:v, about 1.8% w:v, about 1.9% w:v, about 2.0% w:v, about 2.1% w:v, about 2.2% w:v, about 2.3% w:v, about 2.4% w:v, about 2.5% w:v, about 2.6% w:v, about 2.7% w:v, about 2.8% w:v, about 2.9% w:v, about 3.0% w:v, about 3.1% w:v, about 3.2% w:v, about 3.3% w:v, about 3.4% w:v, about 3.5% w:v, or any range in between, inclusive, such as about 0.8% w:v to about 3.0% w:v. For example, in one embodiment, agarose can be initially dissolved into a volume representative of ½ the total volume required to make a final 1% w:v concentration in order to fully dissolve the powder form into a warm gelatinous state. After cooling the mixture to less than 37° C., the remaining ½ volume of conditioned culture media, such as a 50:50 mixture of conditioned fibroblast and osteoblast media, can be added and mixed completely to fully incorporate all components. The matrix of 1% w:v ultra-low melting agarose dissolved in conditioned fibroblast/osteoblast media can be cooled to 4° C. to assist in polymerization of the agarose until further use.

The pharmacokinetic release profile of the biocompatible scaffolds can be first order, zero order, bi- or multi-phasic, to provide the desired therapeutic effect over the desired period of time. A desired release profile can be achieved by using a mixture of polymers having different release rates and/or different percents loading of the component(s) of the composition. Methods for the manufacture of coated-pellets, liposomes, microspheres and microcapsules are well-known in the art.

Once the biocompatible compositions of the present invention are formed, the conditioned cell medium can be about 5%, 10%, 15%, 20%, 25%, 30%, 35%, 40%, 45%, 50%, 55%, 60%, 65%, 70%, 75%, 80%, 85%, 90%, 95%, 99%, or more of the weight, volume, weight to volume, and/or weight to weight, of the total biocompatible composition.

III. BIOCOMPATIBLE COMPOSITION USES AND METHODS

The biocompatible compositions can be used in methods for growing bone or inhibiting bone resorption in a subject, the method comprising administering to a site in need of bone growth and/or bone resorption inhibition in the subject an effective amount of a biocompatible composition of the present invention. Such subjects can have a bone fracture, bone deficiency, metastatic bone disease, osteoarthritis, osteoporosis, and/or osteolytic bone disease. Similarly, the biocompatible compositions can be used in methods of treating a periodontal condition in a subject, the method comprising administering to a periodontal site in need of a) gum and/or bone growth and/or b) gum erosion and/or bone resorption inhibition in the subject an effective amount of a biocompatible composition of the present invention. Useful periodontal conditions that can be treated with the method include, but are not limited to, periodontal disease, gum inflammation, tooth decay, gum disease, gingivitis, and periodontitis. For example, the biocompatible composition can be used as a topically applied periodontal treatment. When using the biocompatible compositions of the present invention according to the described methods, bone mass can be maintained or increased, bone density can be maintained or increased, gum tissue can be maintained or increased, or any combination thereof.

The methods of the present invention generally comprise administering to the subject an effective amount of the biocompatible composition. The methods of the present invention, which are non-surgical, non-invasive and safe, can be used for the treatment and/or prevention of disease states or conditions associated with bone loss, bone degradation, bone deterioration or bone degeneration, including, but not limited to, osteoarthritis, metastatic bone disease, osteolytic bone disease, and dental-related disorders, such as periodontitis, gingivitis, gum disease, and periodontal disease.

The biocompatible compositions provided herein offers physicians a therapeutic alternative/adjunct to shorten recovery times and improve overall patient results with respect to gum and bone regeneration using growth factors. The heterogeneous composition of growth factors released from proliferating fibroblasts and osteoblasts provide a complete source of growth factors to stimulate fibroblast proliferation and differentiation involved in gum regeneration and osteoblast proliferation/maturation involved in bone regeneration, respectively.

The methods of the present invention also relate, at least in part, to the treatment or prevention of oral conditions that would benefit from increased oral osteogenesis including, for example, periodontitis or diseases associated with periodontitis. Biocompatible compositions can be used in methods to increase oral osteogenesis and thereby treat or prevent oral conditions that would benefit from increased oral osteogenesis, such as periodontitis or diseases associated with periodontitis. Such methods involve administering the biocompatible compositions to oral surfaces in need of increased oral osteogenesis. Oral administration is targeted for application to the oral cavity, such as by applying the biocompatible compositions and active ingredients contained therein to surfaces of the oral cavity, including but not limited to salivary glands, saliva, gingiva, dental plaque, teeth, tongue, cheek tissue, and the like. The orally administered agents can be administered alone, or in conjunction with a pharmaceutically acceptable carrier and/or other active ingredients, such as anti-oral disorder that would benefit from increased oral osteogenesis agents, before, after, or simultaneously with the oral composition. Also contemplated by the present invention is the regeneration of other oral tissues including soft tissues, epithelium, and connective tissues, such as collagen and blood vessels.

In general, the biocompatible compositions of the present invention are directly or indirectly applied to a site, such as a bone cavity, periodontal pocket, wound bed, and the like. In some embodiments, the biocompatible composition can be incorporated into a wound dressing. The biocompatible composition can be used as an adjunct with grafts, such as an autograft (skin removed from a patient and reapplied elsewhere on the same patient) or gum flap. The biocompatible composition or pharmaceutical preparation comprising it is physically applied to a contact area of interest, such as a physical pocket or surgical closure, using any of a number of well-known means. For example, a suturing thread can be introduced through the biocompatible composition for incorporation into the surgical site. In some embodiments, the suturing thread can be an absorbable thread, non-absorbable thread, natural thread, synthetic thread, monofilament thread, or multifilament thread. The suturing threads can also be impregnated with germicide substances to prevent the sutures from being contaminated, anticoagulants, or autologous cells to prevent adverse immune reactions.

In another embodiment, the pharmaceutical preparation containing the biocompatible compositions can use bioadhesives to maintain physical contact of the biocompatible composition with the contact surface. These biocompatible adhesives are generally divided into two categories: biological adhesives, synthesized from plasmatic proteins; and synthetic polymers, primarily cyanoacrylate and its derivatives.

As described above, wound dressings, surgical closure, stapling, adhesive strip, bioadhesive, gum flap, and other physical means of restraint can be used to secure the biocompatible composition to the contact surface.

Generally, administration of a therapeutically effective amount of a biocompatible composition or pharmaceutical composition comprising same of the present invention can vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation.

For example, in practicing some embodiments of the present invention, a safe and effective amount of the biocompatible compositions of the present invention can be topically applied to bone, bone surfaces, oral bone, oral bone surfaces, mucosal tissue of the oral cavity, to the gingival tissue of the oral cavity, to the tongue, to the salivary glands, to the saliva, and/or to the surface of the teeth, soft tissues, epithelium, and connective tissues, such as collagen and blood vessels for the treatment or prevention of the above mentioned diseases or conditions of the oral cavity, preferably for at least 1 minute, 2 minutes, 3 minutes, 4 minutes, 5 minutes, 10 minutes, 20 minutes, 30 minutes, 40 minutes, 50 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, 7 days, 8 days, 9 days, 10 days, or longer or any range in between, such as between at least about 10 minutes and at least about 1 hour, between at least about 1 minute and at least about 14 days or longer, and the like. Generally, the biocompatible composition is topically administered within a physical pocket, such as a gum flap or bone defect, and allowed to act until the biocompatible polymer matrix degrades or is otherwise resorbed. The administration methods can be reapplied or repeated from 1 to about 5, preferably from 1 to 3 times per day. Alternatively, or in addition, oral delivery can be performed at a frequency of once to several times per day for up to 12 months, such as once to several times per day for 1, 2, 3, 4, 5, 6, or 7 days; or 1, 2, 3, or 4 weeks; or 1, 2, 3, 4, 5, 6, 7, 8, 9, 10, 11, or 12 months or longer (or any range in between). Typically, the effective amount of the composition is from about 0.5 to about 10 grams, preferably about 1 gram.

In certain embodiments, administration of a prophylactic agent (e.g., biocompatible compositions) can occur prior to the manifestation of symptoms characteristic of the gum loss, gum degeneration, bone loss, bone degradation, bone deterioration, bone degeneration, and the like, including, but not limited to, periodontal disease, osteoarthritis, metastatic bone disease, and osteolytic bone disease, such that a disease or disorder is prevented or, alternatively, delayed in its progression.

Methods of the present invention can be used to prevent, inhibit, or reduce bone loss/resorption. Alternatively or additionally, methods of the present invention can be used to increase, enhance, improve or promote bone growth. For example, certain methods can be used to treat, prevent or delay bone degradation, bone degeneration, and/or bone deterioration; to increase or maintain/stabilize bone mass and/or bone density; and/or to reverse bone loss, bone degradation, bone degeneration and/or bone deterioration. The same applies to periodontal tissues and structures, including gums and periodontal bone.

Methods of the present invention can be used to increase oral osteogenesis and encompass delaying or preventing the onset of such a disease or disorder, reversing, alleviating, ameliorating, inhibiting, slowing down or stopping the progression, aggravation, deterioration or severity of a condition associated with such a disease or disorder.

Treatment with the biocompatible compositions described herein is considered "effective treatment," if any one or all of the signs or symptoms of the bone and/or periodontal disorder that would benefit from increased osteogenesis, enhanced bone growth, and/or reduction of gum/bone loss are altered in a beneficial manner, other clinically accepted symptoms or markers of disease are improved, or even ameliorated, e.g., by at least 10%, 20%, 30%, 40%, 50%, 60%, 70%, 80%, 90%, 95% or more following treatment with the agent. Efficacy can also be measured by a failure of an individual to worsen as assessed by hospitalization or need for medical or dental interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting bone and/or gum loss; or (2) relieving the disease, e.g., increasing bone and/or gum growth; and (3) preventing or reducing the likelihood of the development of a complication from the bone and/or periodontal disorder.

In some embodiments, the biocompatible compositions are provided as an adjunct to periodontal flap surgery. For example, a biocompatible composition of the present invention can be applied to the surgical wound under the flap has been determined herein to have a sustained, post-surgical effect on inducing oral osteogenesis and/or gum regeneration, enhancing bone and/or gum growth, and/or preventing bone and/or gum loss. Periodontal flap surgery is commonly performed to treat chronic periodontal lesions exhibiting significant bone loss in order to debride the lesioned area and remove deposits from the teeth. In general, when patients are not responsive to scaling and root planning procedures and/or antibiotic treatment, periodontal surgery, such as gingivectomy or periodontal flap surgery is often required. Such treatment methods are well-known in the art. For example, in gingivectomy, the dentist reshapes the unhealthy gum tissue in order to reduce the size of the infected pocket. Reduction of the pocket size allows the patient to hygienically maintain the pocket by routine brushing and flossing, thereby eliminating a favorable environment for bacterial growth. Periodontal flap surgery is performed also when scaling and root planning procedures are unsuccessful, especially when there is loss of bone or tissue detachment. In this procedure, incisions are made in the gums and the surrounding alveolar bone is re-contoured to assist in healing of the infected area. Often, surgical treatments are insufficient in stimulating re-growth or replacement of the destroyed bone and cementum caused by severe periodontal disease such that the adjunct method using the biocompatible compositions described herein are especially useful. As described above, however, the biocompatible compositions of the present invention can be applied or administered to any bone or periodontal structure in need thereof whether associated with periodontal flap surgery or not.

The effectiveness of any oral composition described herein to treat a bone and/or periodontal disorder can be monitored by comparing two or more samples obtained from a subject undergoing treatment. In general, it is preferable to obtain a first sample from the subject prior to beginning therapy and one or more samples during treatment. In such a use, a baseline of expression of cells from subjects with the oral disorder prior to therapy is determined and then changes in the baseline state of expression of cells or detection of bone growth from subjects with the oral disorder that would benefit from increased oral osteogenesis, enhanced bone growth, and/or reduction of bone loss is monitored during the course of therapy. Alternatively, two or more successive samples obtained during treatment can be used without the need of a pre-treatment baseline sample.

Whether one or more bone and/or periodontal disorder(s) in a subject undergoing therapy are being ameliorated can be determined according to well-known assays in the art. For example, the following indicators can be monitored: 1) increase in gum/bone growth and/or gum/bone density; 2) decrease in gum/bone loss and/or reversal of gum/bone density loss; 3) decrease in tooth movement; 4) increase in gum, osteoblast, or bone-specific genes, such as alkaline phosphatase (ALP), collagen type I, osteocalcin, osteopontin, Cbfa1/Runx2, gsc, Dlx1, DlxS, Msx1, Cart1, Hoxa1, Hoxa2, Hoxa3, Hoxb1, rae28, Twist, AP-2, Mf1, Pax1, Pax3, Pax9, TBX3, TBX4, TBXS, and Brachyury (as determined by gene expression, enzymatic activity, immunohistochemistry, and the like; Olsen et al. *Annu. Rev. Cell. Dev. Biol.* (2000) 16:191); 5) decrease in periodontal pocket size; 6) increase in gum attachment level; 7) decreased tooth loss; 8) decreased periodontal inflammation; 9) decrease in periodontal disease progression stage; and combinations thereof.

In the methods of the present invention, biocompatible compositions can be administered prior to the onset of a pathophysiological condition associated with bone loss for a prophylactic action, or they can be administered after initiation of the condition for a therapeutic action.

Generally, the vertebrate subject (human or other mammal) that can be treated using methods of the present invention suffer from a disease or condition associated with bone loss or are susceptible to a disease or condition associated with bone loss (e.g., exhibit a high or higher risk of developing such a disease or condition, or have been diagnosed with a disease state or condition that is known to cause, to result in or to be associated with bone loss).

Disease states and conditions associated with bone loss that can be treated and/or prevented using the inventive methods include any condition that is characterized by, is accompanied with, is associated with, results in, or induces bone degradation, bone deterioration or bone degeneration, for example leading to loss in bone mass and/or loss in bone density. Examples of such conditions include, but are not limited to, periodontal disease such as periodontitis; bone fracture or deficiency; osteoarthritis; metastatic bone disease; and osteolytic bone disease. Other examples of such conditions include, without limitation, cancers and tumors (such as osteosarcoma and multiple myeloma), renal disease (including acute renal failure, chronic renal failure, renal bone dystrophy and renal reperfusion injury), kidney disease, and premature ovarian failure. Thus, the methods of the present invention can be used for preventing bone loss, for filling in bone defects, stimulating rapid fusion of bone fractures, grafts, and bone-prostheses, and promoting strengthening of osteoporotic bones.

In certain methods of the present invention, the biocompatible compositions are administered in combination with at least one therapeutic agent that that a) promotes gum and/or bone growth and/or b) inhibits gum erosion and/or bone resorption. For example, such an agent can be a bone morphogenetic factor, an anti-resorptive agent, an osteogenic factor, a cartilage-derived morphogenetic protein, a growth hormone, an estrogen, a biphosphonate, a statin, a differentiation factor, or combinations thereof.

In some methods of the present invention, the biocompatible compositions are administered in combination with one or more additional therapeutic agents. Examples of additional therapeutic agents include, but are limited to, analgesics, anesthetics, antimicrobial agents, antibacterial agents, antiviral agents, antifungal agents, antibiotics, anti-inflammatory agents, antioxidants, antiseptic agents, immunostimulating agents, and combinations thereof. For example, such agents can be antimicrobial compounds and/or non-steroidal anti-inflammatory agents (NSAIDs). In certain embodiments, the additional therapeutic agent or agents are COX-2 inhibitors, such as selective COX-2 inhibitors, e.g., celecoxib, rofecoxib, and/or valdecoxib. In such embodiments, the biocompatible compositions and other agents can be administered sequentially or simultaneously.

Alternatively, or additionally, the biocompatible compositions can be administered in combination with (i.e., prior to, concomitant with, and/or following) a medical procedure. For example, the medical procedure can be a surgical intervention to eliminate a periodontal pocket and/or to recontour the bone, or a selective reshaping of tooth surfaces in a subject suffering from a periodontal disease. Alternatively, the medical procedure can be bone grafting, surgical tumor removal, and the like.

Such additional agents can be those naturally present within the body and/or that is naturally secreted at a site undergoing bone growth/formation and plays a role in one or more steps of the bone formation process. As will be apparent to those of ordinary skill in the art, variants, synthetic analogs, derivatives, and active portions of these agents or biomolecules can, alternatively, be used in the inventive compositions as long as they exhibit substantially the same type of property/activity as the native biomolecule. Such variants, synthetic analogs, derivatives or active portions are intended to be within the scope of the term "therapeutic biomolecule".

Therapeutic agents or biomolecules can be extracted from mammalian tissues and used in the present invention either crude or after purification. Alternatively, they can be prepared chemically or by conventional genetic engineering techniques, such as via expression of synthetic genes or of genes altered by site-specific mutagenesis.

Therapeutic agents or biomolecules that increase bone mass or bone density include, but are not limited to, growth factors (such as IGF-1, IGF-2, macrophage growth factor, platelet derived growth factors (PDGFs), fibroblast growth factors (FGFs), epidermal growth factors (EGFs), transforming growth factors (TGFs), cartilage-derived morphogenic protein (CDMP-1, CDMP-2, CDMP-3) and connective tissue activating peptides (CTAPs), minerals (such as calcium, aluminum, strontium and fluoride), vitamins (such as Vitamin D3), hormones (such as parathyroid hormone (PTH), and parathyroid hormone related protein (PTHrP)); prostaglandins (such as PDG1, PDG2, PGE2, PGE1 and PGF2); inhibitors of 15-lipoxygenase; dexamethasone; statins; and bone morphogenic proteins (such as BMP-2, BMP-4 and BMP-7).

In certain embodiments, the therapeutic agent or biomolecule can be a transforming growth factor beta (TGF-β). TGF-βs are extracellular polypeptides that are implicated in a broad range of biological processes (J. Massague, *Annu. Rev. Cell. Biol.* (19900 6: 597-641) and play a central role in key events during embryogenesis, adult tissue repair, and immunosuppression (M. B. Sporn et al. *Cell. Biol.* (1992) 119: 1017-1021; S. W. Wahl, *J. Clin. Immunol.* (1992) 12: 61-74; D. M. Kingsley, *Genes Dev.* (1994) 8: 133-146). TGF-β is known to evoke proliferation and differentiation of osteoblasts (M. Centrella et al., *J. Bone Join. Surg.* (1991) 73: 1418-1428; T. A. Mustoe et al. *Science,* 1987, 237: 1333-1336; L. S. Beck et al. *J. Bone Miner. Res.* (1991) 6: 961-968). TGF-β is also known to play an important role in the early phase of osteogenesis (S. Dieudonne et al. *J. Cell. Biochem.* (1999) 76: 231-243). TGF-β to be used in the inventive compositions can be produced from recombinant cell cultures. Alternatively, TGF-β can be derived from blood platelets or any other mammalian tissue using any suitable method. Preferably, TGF-β is derived from human tissue. However, since TGF-β is not species specific, it can, alternatively, be derived from animal sources such as bone or porcine sources. In certain cases, TGF-β is preferably purified to essential homogeneity using, for example, sequential gel filtration, cation-exchange chromatography, or high performance liquid chromatography.

In other embodiments, the therapeutic agent or biomolecule is a bone morphogenic protein (BMP). BMP is a bone-forming protein that has been reported to stimulate pluripotential cells to be differentiated into chondrocytes and osteogenesis cells, and to play an important role in bone regeneration (M. R. Urist *Science* (1965) 150: 893-899; M. R. Urist et al *J. Dent. Res.* (1971) 50: 1392-1406; J. M. Wozney *Mol. Reprod. Dev.* (1992) 32: 160-167; J. M. Wozney et al. *Science* (1988) 242: 1528-1534; I. One et al. *Craniofac. Surg.* (1996) 7: 418-425). BMPs that can be used in the present invention include, but are not limited to, BMP-1, BMP-2.alpha., BMP-2β, BMP-2β, MP-4, BMP-5, BMP-6, BMP-7, BMP-8β, BMP-9, BMP-10, BMP-11, BMP-12, BMP-13, BMP-14, and BMP-15.

In still other embodiments, the composition comprises sources of calcium and phosphate to locally enhance the soluble concentration of dissolved calcium ($Ca^{2+}$) and phosphate ($PO_4^{-1}$) within and around the site of application of the composition. The calcium source and the phosphate source can be the same material or can be different materials. Suitable sources of calcium for use in the present invention include any acidic calcium salt, such as calcium phosphate salts (e.g., monocalcium phosphate, calcium phosphate dihydrate (also known as dical), and calcium pyrophosphate) or calcium citrate salts. Suitable sources of phosphate for use in the present invention include any phosphate salt, such as calcium phosphate salts (e.g., acidic calcium phosphate salts) and sodium phosphate salts. Examples of acidic calcium phosphate salts include hydrogen phosphate dihydrate, monocalcium phosphate, and calcium pyrophosphate.

In yet other embodiments, the therapeutic agent or biomolecule is a statin. The terms "statins" and "HMG-CoA reductase inhibitors" are used herein interchangeably and refer to compounds that inhibit the enzyme 3-hydroxy-3-methylglutaryl coenzyme A (HMG-CoA) reductase. HMG-CoA reductase is the principal rate-limiting enzyme involved in cellular cholesterol biosynthesis. Statins enhance the production of osteoblasts, the cells that produce new bone, and enhance osteoblast differentiation (E. Harris et al. *Mol. Cell. Diff.* (1995) 3: 137-147; G. Mundy etal., *Science* (1999) 286: 19464949). In particular, statins have been shown to promote BMP production systematically or in fracture sites (U.S. Pat. Nos. 6,022,887; 6,080,779; and 6,376,476). Examples of statins suitable for use in the present invention include, but are not limited to, lovastatin, pravastatin, velostatin, simvastatin, fluvastatin, cerivastatin, mevastatin, dalvastatin, fluindostatin, atorvastatin, a prodrug thereof, or a physiologically acceptable salt thereof.

Agents that prevent bone loss/resorption that can be used in the present invention include, but are not limited to, progestins, estrogen, estrogen/progestin combinations, estrone, estriol, 17α- or 17β-ethynyl estradiol, SB242784, polyphosphonates, and bisphosphonates. Commercially available bisphosphonates include, etidronate, clodronate, tiludronate, alendronate, pamidronate, and ibandronate.

In some embodiments, agents that promote angiogenesis in tissues and/or agents that are useful in treating surfaces of mucous membranes after surgery or injury, are useful.

Analgesics suitable for use in the present invention include non-steroidal, anti-inflammatory drugs (NSAIDs). NSAIDs have analgesic, antipyretic and anti-inflammatory activity. They act peripherally to provide their analgesic effect by interfering with the synthesis of prostaglandin, through cyclooxygenase (COX) inhibition. There are many different types of NSAIDs, including aspirin and other salicylates. Representative examples include, but are not limited to, ibuprofen, naproxen, sulindac, diclofenac, piroxicam, ketoprofen, diflunisal, nabumetone, etodolac, oxaprozin, and indomethacin. Several of the more potent NSAIDs have been developed into topical products for local applications to painful areas of the body.

Anesthetics, such as xylocaine, lidocaine or benzocaine (or other drugs such as those described below) can be added to an analgesic compositions of the present invention to provide an immediate but short-term pain relief until the analgesic agent becomes fully effective. Anesthetics that are suitable for use in the practice of the present invention include sodium-channel blockers. Sodium-channel blockers prevent the generation and conduction of nerve impulses by decreasing or preventing the large transient increase in the permeability of excitable membranes to sodium ions, $Na^+$.

Examples of sodium-channel blockers include, but are not limited to, ambucaine, amolanone, amylcaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dyclonine, ecogonidine, ecogonine, etidocaine, euprocin, fenalcomine, formocaine, hexylcaine, hydroxyteteracaine, isobutyl p-aminobenzoate, leucinocaine, levoxadrol, lidocaine, mepivacaine, meprylcaine, metabutoxycaine, methyl chloride, myrtecaine, naepaine, octacaine, orthocaine, oxethazaine, parenthoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, and active derivatives, prodrugs, analogs, pharmaceutically acceptable salts, or mixtures thereof.

The biocompatible compositions of the present invention can also be combined, or used in conjunction with anti-infective agents, encompassing compounds, molecules or drugs, which have an anti-infective activity (i.e., they can decrease the risk of infection, prevent infection, or inhibit, suppress, combat or otherwise treat infection). In certain embodiments, these compounds, molecules or drugs have an anti-infective activity when applied topically. Anti-infective agents suitable for use in the present invention include, but are not limited to, antiseptics, antimicrobial agents, antibiotics, antibacterial agents, antiviral agents, antifungal agents, antiprotozoan agents, immunostimulating agents, and any combinations thereof.

Antiviral agents can be present in compositions to prevent viral infection and/or to reduce viral titers at a site. Suitable antiviral agents include RNA synthesis inhibitors, protein synthesis inhibitors, immunostimulating agents, and protease inhibitors. Antiviral agents can, for example, be selected from the group consisting of acyclovir, amantadine hydrochloride, foscarnet sodium, ganeiclovir sodium, phenol, ribavirin, vidarabine, and zidovudine.

Antifungal agents can be selected from a wide variety of therapeutic agents. For example, lactic acid (i.e., 2-hydroxypropanoic acid) is an antifungal agent that is known to inhibit the growth of pathogens. Sorbic acid (i.e., 2,4-hexadienoic acid) is a natural antifungal agent that kills *Candida albicans*. Other antifungal agents include, but are not limited to, Amphotericin B, Ciclopirox, Clotrimazole, Enilconazole, Econazole, Fluconazole, Griseofulvin, Halogropin, Introconazole, Ketoconazole, Miconazole, Naftifine, Nystatin, Oxiconazole, Sulconazole, Thiabendazole, Terbinafine, Tolnaftate, Undecylenic acid, Mafenide, Silver Sulfadiazine, and Carbol-Fushsin.

Antibiotics and other antimicrobial agents can be selected from the group consisting of bacitracin; the cephalosporins (such as cefadroxil, cefazolin, cephalexin, cephalothin, cephapirin, cephradine, cefaclor, cefamandole, cefonicid, ceforanide, cefoxitin, cefuroxime, cefoperazone, cefotaxime, cefotetan, ceftazidime, ceftizoxime, ceftriaxone, and meropenem); cycloserine; fosfomycin, the penicillins (such as amdinocillin, ampicillin, amoxicillin, azlocillin, bacamipicillin, benzathine penicillin G, carbenicillin, cloxacillin, cyclacillin, dicloxacillin, methicillin, mezlocillin, nafcillin, oxacillin, penicillin G, penicillin V, piperacillin, and ticarcillin); ristocetin; vancomycin; colistin; novobiocin; the polymyxins (such as colistin, colistimathate, and polymyxin B); the aminoglycosides (such as amikacin, gentamicin, kanamycin, neomycin, netilmicin, paromomycin, spectinomycin, streptomycin, and tobramycin), the tetracyclines (such as demeclocycline, doxycycline, methacycline, minocycline, and oxytetracycline); carbapenems (such as imipenem); monobactams (such as aztreonam); chloramphenicol; clindamycin; cycloheximide; fucidin; lincomycin; puromycin; rifampicin; other streptomycins; the macrolides (such as erythromycin and oleandomycin); the fluoroquinolones; actinomycin; ethambutol; 5-fluorocytosine; griseofulvin; rifamycins; the sulfonamides (such as sulfacytine, sulfadiazine, sulfisoxazole, sulfamethoxazole, sulfamethizole, and sulfapyridine); and trimethoprim.

Other suitable antibacterial agents include, but are not limited to, bismuth containing compounds (such as bismuth aluminate, bismuth subcitrate, bismuth subgalate, and bismuth sub salicylate); nitrofurans (such as nitrofurazone, nitrofurantoin, and furozolidone); metronidazole; tinidazole; nimorazole; and benzoic acid.

Antiseptic agents can be selected from the group consisting of benzalkonium chloride, chlorhexidine, benzoyl peroxide, hydrogen peroxide, hexachlorophene, phenol, resorcinol, and cetylpyridinium chloride.

Immunostimulating agents suitable for use in the inventive compositions can be selected from a wide range of therapeutic agents, such as interleukin 1 agonists, interleukin 2 agonists, interferon agonists, RNA synthesis inhibitors, and T cell stimulating agents.

Anti-inflammatory agents for use in the present invention are compounds, molecules or drugs which have an anti-inflammatory activity (i.e., they can prevent or reduce the duration and/or severity of inflammation; prevent or reduce injury to tissue; and/or provide relief from at least one of the manifestations of inflammation such as erythema, swelling, tissue ischemia, fever, and the like). In certain embodiments, these compounds, molecules or drugs have an anti-inflammatory activity when applied topically.

Anti-inflammatory agents suitable for use in the present invention can be selected from a wide variety of steroidal and non-steroidal anti-inflammatory agents. Examples of NSAIDs can be found above. Examples of steroidal anti-inflammatory agents include, but are not limited to, aclomethasone dipropionate, flunisolide, fluticasone, budesonide, triamcinolone, triamcinoline acetonide, beclomethasone diproprionate, betamethasone valerate, betamethasone diproprionate, hydrocortisone, cortisone, dexamethason, mometasone furoate, prednisone, methylprednisolone aceponate, and prednisolone.

Anti-inflammatory agents can, alternatively or additionally, be selected from the wide variety of compounds, molecules, and drugs exhibiting antioxidant activity. Antioxidants are agents that can prevent or reduce oxidative damage to tissue. Antioxidants can be selected from the group consisting of vitamin A (retinal), vitamin B (3,4-didehydroretinol), vitamin C (D-ascorbic acid, L-ascorbic acid), α-carotene, β-carotene, γ-carotene, δ-carotene, vitamin E (α-tocopherol), β-tocopherol, γ-tocopherol, δ-tocopherol, tocoquinone, tocotrienol, butylated hydroxy anisole, cysteine, and active derivatives, analogs, precursors, prodrugs, pharmaceutically acceptable salts or mixtures thereof.

The amount of therapeutic agent(s) osteogenic factors, growth hormones, analgesic, anti-inflammatory agents present in a composition of the invention can vary depending upon the dosage recommended or permitted for the particular therapeutic agent, as well as the type of bone loss being treated and the presence and nature of other ingredients/components in the composition. In certain embodiments, the amount of therapeutic agent present is the ordinary dosage required to obtain the desired result through topical administration. Such dosages are either known to or readily determined by the skilled practitioner in the pharmaceutical or medical arts.

In some embodiments, conditioned cell media and biocompatible compositions of the present invention are formulated as a pharmaceutical composition by admixing a pharmaceutically acceptable carrier or excipient. Pharmaceutical composition comprising the biocompatible compositions of the present invention can be formulated according to general pharmaceutical practice (see, for example, "Remington's Pharmaceutical Sciences" and "Encyclopedia of Pharmaceutical Technology", J. Swarbrick, and J. C. Boylan (Eds.), Marcel Dekker, Inc: New York, 1988). For example, a "pharmaceutically-acceptable carrier" refers to a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In some embodiments, the conditioned cell media can be used alone without formulation with the biocompatible polymer matrix. In some embodiments, the conditioned cell medica can be used in a formulation with the biocompatible polymer matrix. Whether the conditioned cell media is used alone or with the biocompatible polymer, the resulting compositions can be used alone, such as by direct administration to a delivery site of interest. Alternatively, in some embodiments, whether the conditioned cell media is used alone or with the biocompatible polymer, the resulting compositions can be used in a formulation with and/or within an additional matrix material. The choice of matrix material is based on biocompatibility, biodegradability, mechanical properties, cosmetic appearance and interface properties. Representative, non-limiting matrices encompass biodegradable and chemically defined materials, including calcium sulfate, tricalciumphosphate, hydroxyapatite, polylactic acid, and polyanhydrides. Other matrix materials are biodegradable and biologically well defined, such as bone or dermal collagen. Other matrices are comprised of pure proteins or extracellular matrix components. Other representative matrices are nonbiodegradable and chemically defined, such as sintered hydroxyapatite, bioglass, aluminates, or other ceramics. Matrices can be comprised of combinations of any of the above-mentioned types of material, such as polylactic acid and hydroxyapatite or collagen and tricalciumphosphate. The bioceramics can be altered in composition, such as in calcium-aluminate-phosphate and processing to alter pore size, particle size, particle shape, and biodegradability. Without being bound by theory, it is believed that the conditioned cell media formulated with the biocompatible polymer matrix encompassed by the present invention allows for substantially less matrix material to be used in order to result in bone growth (e.g., total osseointegration, vertical osseointegration, lateral osseointegration, and the like) and/or inhibition of bone resorption as compared against the conditioned media without the biocompatible polymer matrix due to the ability of the biocompatible polymer matrix to modulate the release of the conditioned cell media over time. For example, in some embodiments, the capacity of the composition for having a desired effect on bone including joining with juxtaposed bone and other tissue (i.e., osseointegration) is maintained using as little as 5%, 10%, 15%, 20%, 25%, 30%, 31%, 32%, 33%, 1/3, 34%, 35%, 36%, 37%, 38%, 39%, 40%, 45%, 50%, 55%, 60%, 65%, 70%, 75%, 80%, 85%, 90%, or any range in between, inclusive, such as 30%-40%, as compared against compositions without the biocompatible polymer.

IV. KITS

In another aspect, the present invention provides kits comprising a biocompatible composition or pharmaceutical composition comprising same of the present invention. In certain embodiments, the biocompatible composition is provided with at least one therapeutic agent in the kit. The at least one therapeutic agent can be provided separately or as a mixture.

For example, a kit can comprise two separate containers, with the first container comprising the biocompatible compositions thereof, and the second container comprising the therapeutic agent or a composition thereof. A kit can alternatively comprise two separate containers, with the first container comprising a mixture or composition comprising the biocompatible compositions and therapeutic agent, and the second container comprising a suitable medium intended to be added to the first container before use in order to obtain a ready-to-use composition. Alternatively, or additionally, a kit can be composed of a container comprising a mixture or composition comprising the biocompatible compositions and therapeutic agent and a tool (e.g., brush, syringe, spatula) to be used to apply the mixture or composition of the first composition.

In certain embodiments, the individual containers (e.g., vials, ampoules, flasks, bottles, tubes with a narrow tips) are maintained in close confinement for commercial use.

A kit can further comprise instructions for using the biocompatible compositions and therapeutic agent (and any other additional agents and reagents) according to the present invention. Instructions for using the kit according to one or more methods of the invention can comprise information about the indications, preferred mode(s) of administration, preferred regimen(s), preferred dosages, potential side effects, and the like. The kits can also comprise a notice in the form prescribed by a government agency (e.g., FDA) regulating the manufacture, use or sale of pharmaceuticals. An identifier, e.g., a bar code, radio frequency, ID tags, etc., can be present in or on the kit. The identifier can be used, for example, to uniquely identify the kit for purposes of quality control, inventory control, tracking movement between workstations, etc. In certain embodiments of the present invention, the kits can be manufactured in accordance with good manufacturing practices as required by government agency (e.g., FDA) approved pharmaceuticals.

EXEMPLIFICATION

This invention is further illustrated by the following examples, which should not be construed as limiting.

Example 1: Materials and Methods for Exmaples 2-3

A. In Vitro Studies

Human primary neonatal dermal fibroblasts and human primary osteoblasts were used in this study. For fibroblasts, approximately 500 milliliters (mL) of DMEM basal cell culture media contains fetal bovine serum (FBS) (4.6% v:v), GlutaMax™ (1.1% v:v), recombinant human epidermal growth factor (2.25 micrograms), and recombinant human fibroblast growth factor basic (0.68 micrograms). Osteoblast primary media contains, for approximately 500 mL of total volume, DMEM basal cell culture media supplemented with ascorbic acid (2.75 mg), GlutaMax™ (1% v:v), and FBS (9.8% v:v).

The fibroblast media (media A) and osteoblast media (media B) were added to proliferating fibroblasts and osteoblasts, respectively, and the cell cultures were incubated in a humidified chamber at 37° C. at 5% $CO_2$ for a duration of 24 hrs before harvesting. Conditioned cell media (media C) was generated as a 50:50 mixture of fibroblast- and osteoblast-conditioned media.

B. Polymer Matrix

The polymer matrix comprises ultra-low melting agarose (SeaPrep™ Agarose from Lonza) at a concentration of 1% w:v, agarose was initially dissolved into a volume representative of ½ the total volume required to make a final 1% w:v concentration in order to fully dissolve the powder form into a warm gelatinous state. After cooling the mixture to less than 37° C., the remaining ½ volume of media C (50:50 mixture of conditioned fibroblast and osteoblast media) was added and mixed completely to fully incorporate all components. The matrix of 1% w:v ultra-low melting agarose dissolved in conditioned fibroblast/osteoblast media was cooled to 4° C. to assist in polymerization of the agarose until further use.

C. Morphology

Osteoblasts were seeded on 6-well plates in basal osteoblast growth media overnight. Media was aspirated and adherent cells washed with dPBS before adding respective media. Cells were grown for an additional 24 hrs before observing at 10× using an Olympus CK2 inverted microscope.

D. Cell Proliferation Assay

The CellTiter 96® AQueous One Solution Cell Proliferation Assay was used to determine the number of viable cells at 24 hr and 48 hr timepoints. Briefly, approximately $2 \times 10^4$ cells were plated overnight onto a 96-well plate in primary osteoblast growth media. After allowing cells to seed for 24 hrs, the growth media was aspirated and washed with dPBS. After aspirating the dPBS, 100 μl of respective media was added to individual wells. Assay timepoints were approximately 24 hrs and 48 hrs after the addition of the respective growth media. Absorbance at 490 nm was recorded as a function of cell growth.

E. Scratch Assay

Osteoblast cells were seeded on 6-well plates in basal fibroblast growth media overnight. A pipette tip was used to make a physical separation in each confluent well. Basal media was then aspirated followed by washing with dPBS. The respective media was then added to the respective well and allowed to grow for an additional 24 hrs. Images were obtained using an Olympus CK2 inverted microscope.

F. In Vivo Studies

All animal experiments were conducted according to the Columbia University ILAR guide for the care and use of laboratory animals and the animal welfare act regulations administered by the United States Department of Agriculture. As required by the animal welfare act regulations, all experimental procedures were approved by IACUC.

A total of 8 canines were utilized for the study. In each canine subject, a total of 8 defects as defined as dental extractions/implant sites were used. The 8 defects were divided into 2 groups as follows: group 1: vertical bone defect (5 mm)+4 implants+bone grafting and group 2: vertical bone defect (5 mm)+4 implants+bone grafting+ (growth factors; DentaPro: fibroblast/osteoblast-conditioned media alone without low melting point agarose as described above in Example 1, PeriOSM: fibroblast/osteoblast-conditioned media+low melting point agarose as described above in Example 1).

Animal subjects underwent a series of 3 total surgeries. In particular, the initial surgery consisted of tooth extractions followed by 12 weeks of healing to allow for complete healing of extraction sockets. This was followed by a second surgical procedure to create a standardized bone defect (20×5 mm; length×height) and the insertion of a bone implant and bone grafting materials (hydroxyapatite) with or without growth factors. Animals were sacrificed at 4- and 8-week timepoints as measured post-implant insertion/bone defect and analyzed via micro-computed tomography (micro CT) and standard histological processes.

Example 2: Biocompatible Compositions Positively Affect Cells

In order to analyze paracrine-like effects of the agarose, solidified agarose at a concentration of 1% w:v was cut into 1 cm. diameter discs. In single wells of a 6-well plate, 3 discs containing either PBS, unconditioned media, or conditioned media, were respectively placed together, but spaced apart from each other in the same well and allowed to adhere before adding osteoblast cells. Basal, unconditioned osteoblast media was added to cover the cells but did displace the agarose disc. Cells were allowed to grow for 24 hrs at 37° C. and 5% $CO_2$. Images were then taken to observe cell behavior around the respective discs.

The solidified agarose discs containing conditioned media, were generated as follows: Briefly, agarose was initially heated in a volume of ddH2O representative of ½ the total volume required to make a final 1% w:v concentration in order to fully dissolve the powder form into a warm gelatinous state. After cooling the mixture to less than 37° C., the remaining ½ volume of conditioned culture media, such as a 50:50 mixture of conditioned fibroblast and osteoblast media, was added and mixed completely to fully incorporate all components. The matrix of 1% w:v ultra-low melting agarose dissolved in conditioned fibroblast/osteoblast media was then poured into petri dishes to a thickness of up to 1 cm. The dishes were then cooled to 4° C. to assist in polymerization of the agarose until further use. After allowing the agarose discs to solidify, circular discs up to a diameter of 1.5 cm were isolated for further experiments.

When comparing unconditioned to conditioned media, there was no discernible difference in cell size or morphology (FIG. 1). There is a significant difference between the negative control of DPBS as compared to the other two media (i.e., unconditioned and conditioned media).

Figure 2:
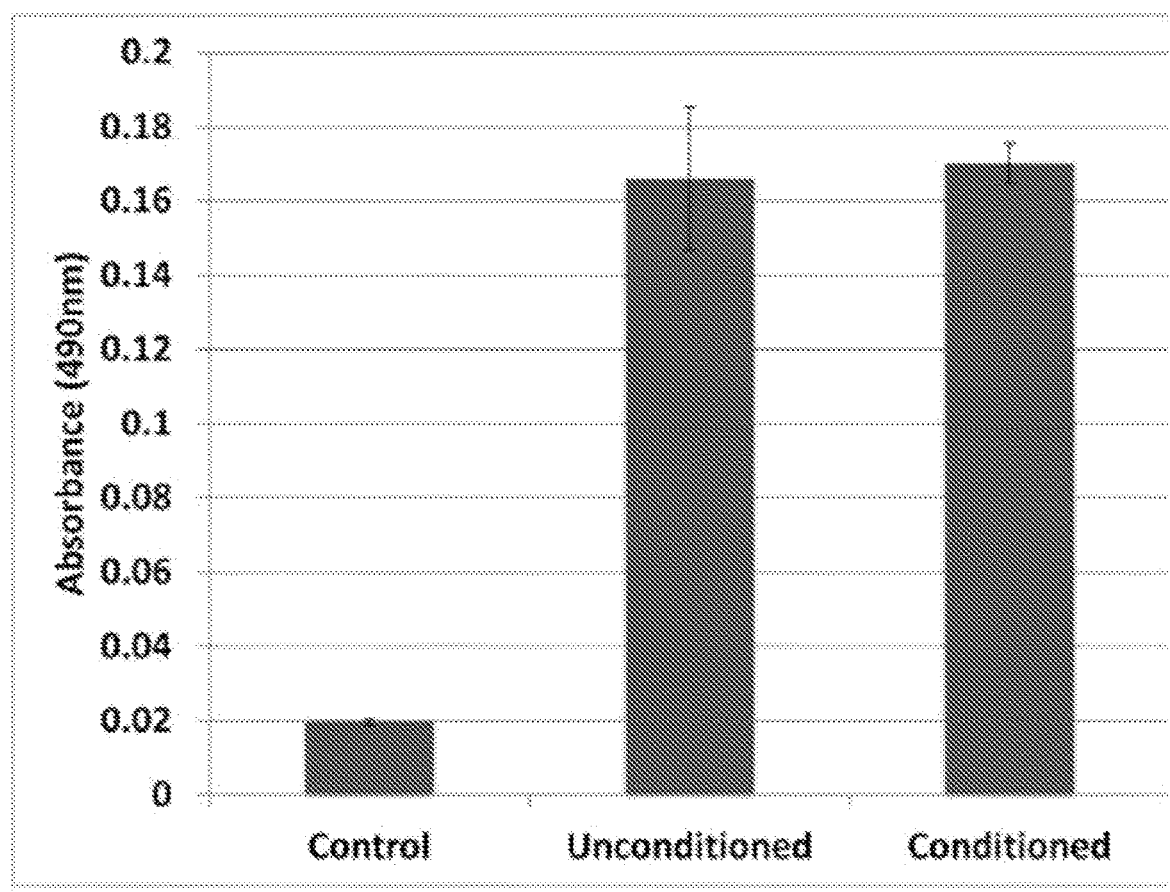
FIG. 2 shows cell proliferation assay after 24 hours (hrs). The control media corresponds to DPBS. The unconditioned media corresponds to 50:50 mixtures for unconditioned fibroblast and osteoblast media. The conditioned media corresponds to a 50:50 mixture of fibroblast and osteoblast conditioned media.

Based on a fluorescence based assay, the conditioned media resulted in the highest level of cell proliferation as compared to unconditioned and control media (FIG. 2).

Figure 3A:
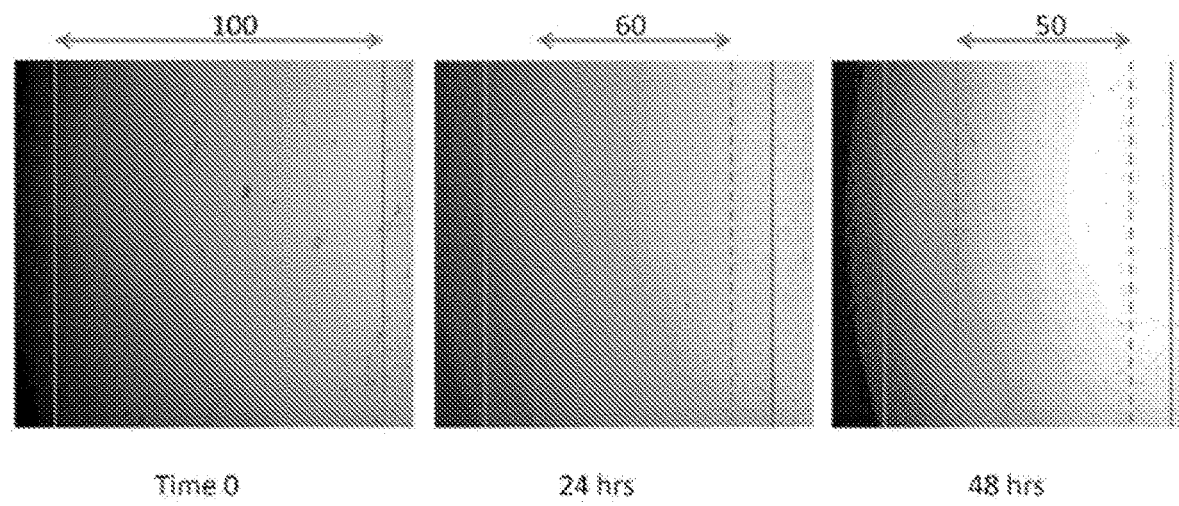
FIGS. 3A and 3B show photomicrographs of scratch assays.
Figure 3B:
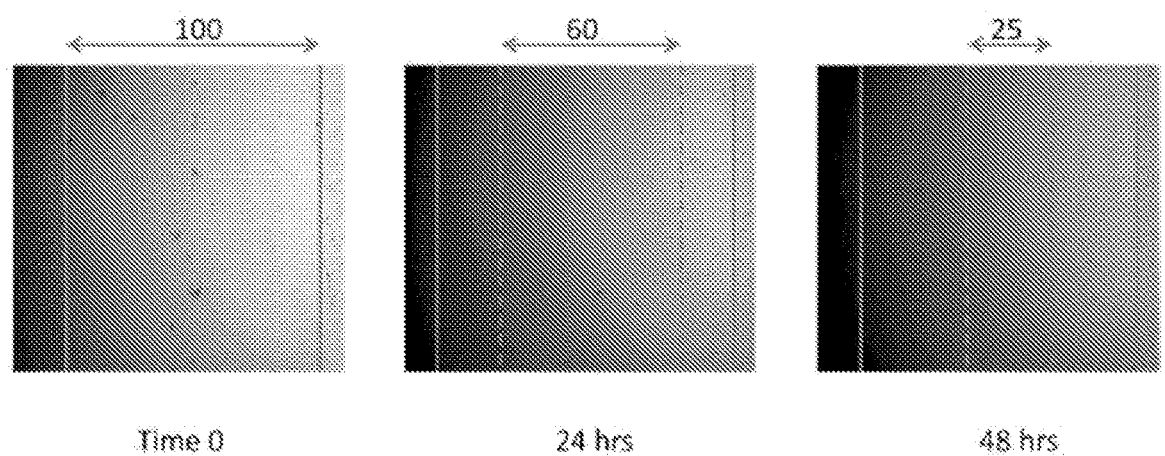

Osteoblast conditioned media as opposed to unconditioned media resulted in an accelerated wound healing (FIG. 3).

Figure 4:
FIG. 4 shows photomicrographs of paracrine-like effects of agarose discs on neighboring cells at 24 hr. Agarose discs containing conditioned media had significantly more cell aggregation around the periphery as compared to control (PBS) or unconditioned (unconditioned media).

Agarose infused with conditioned media appears to exert a stronger chemoattractant effect possibly due to passive diffusion of growth factors release from the matrix (FIG. 4). This characteristic represents an important feature with respect to the clinical application of the biocompatible compositions described herein and their ability to fill a physically voided space (e.g., between dental implant and adjacent gum line) and to stimulate cells to migrate towards the polymer matrix of the biocompatible compositions. As the polymer matrix dissolves, cells from either side of the polymer matrix can come together.

Example 3: Periodontal Effects of Biocompatible Compositions In Vivo

Figure 5:
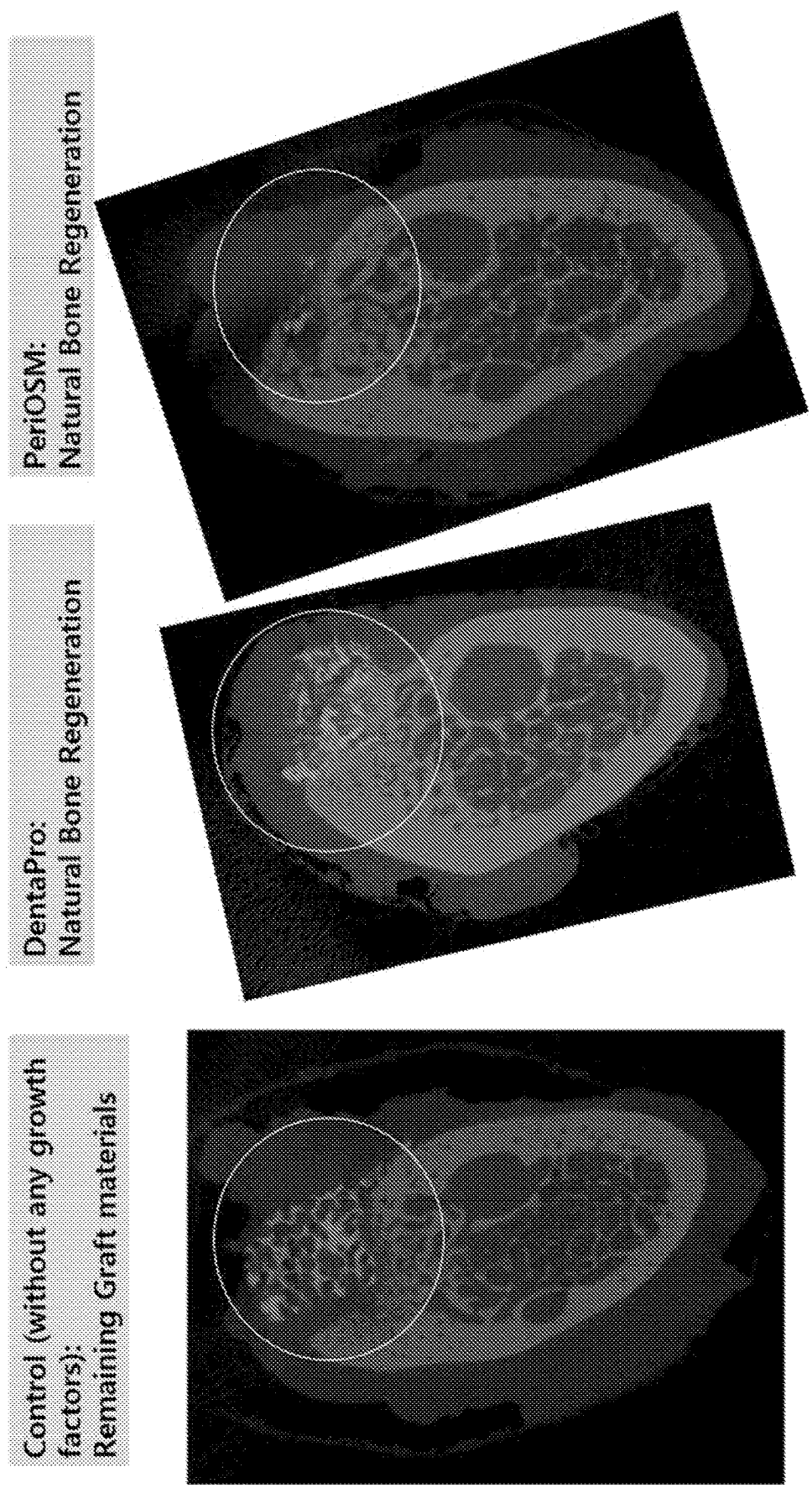
FIG. 5 shows micro CT section scan images of bone regeneration after 8 weeks of treatment.
Figure 6:
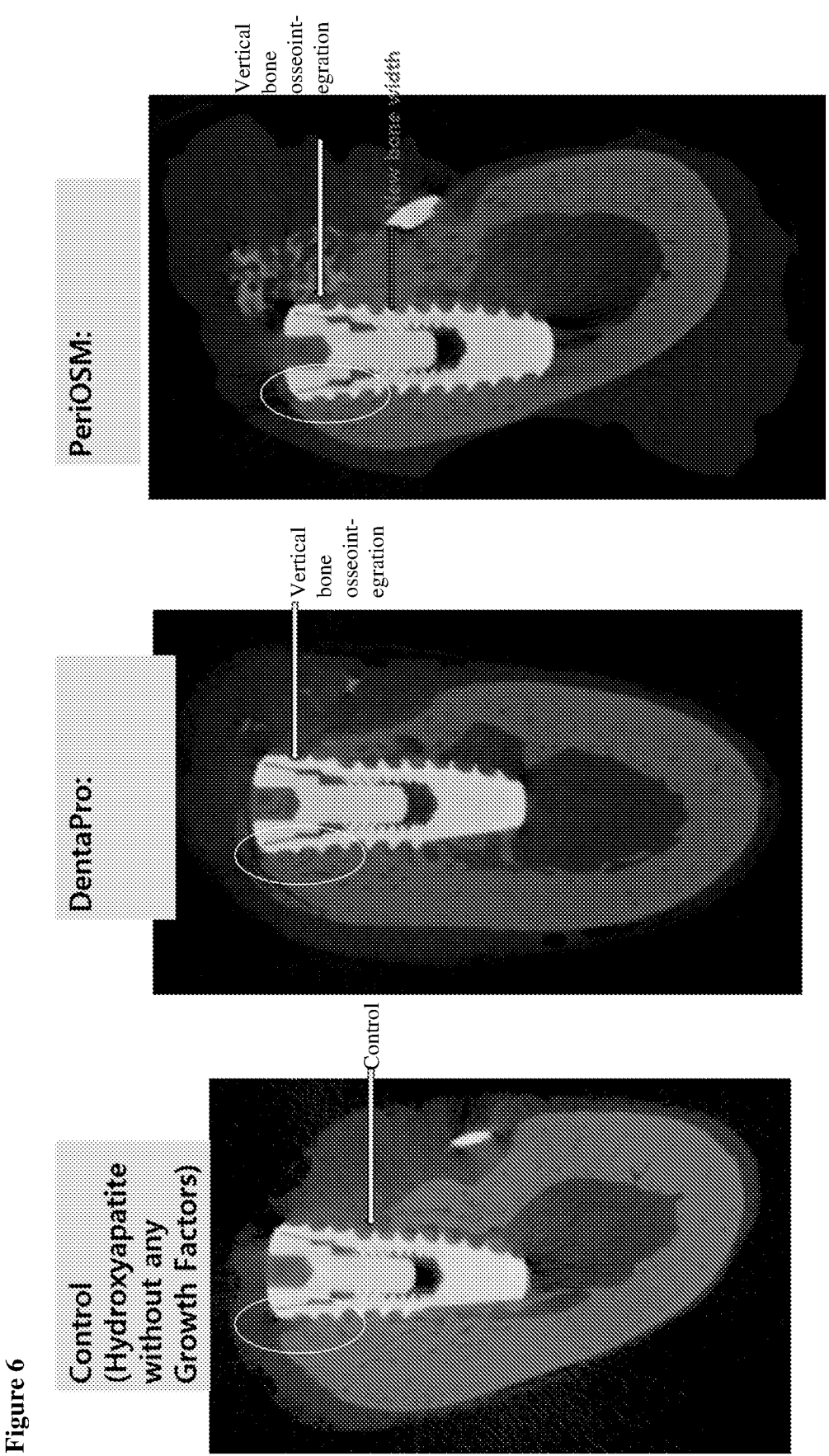
FIG. 6 shows micro CT section scan images of bone growth and implant-bone osseointegration after 8 weeks of treatment.

In vivo studies were performed in order to assess the effects of DentaPro and PeriOSM on new bone regeneration and dental implant osseointegration using canine animal models in which right (control) and left (experimental) side mandibular premolar areas were used. FIG. 5 shows significant bone regeneration using DentaPro and PeriOSM as compared to control after 8 weeks. Similarly FIG. 6 shows the results of implant osseointegration (e.g., differences in bone growth and implant-bone integration height) after 8 weeks. In particular, FIG. 6 demonstrates that treatment with both DentaPro and PeriOSM showed significant osseointegration (circle) compared to the control. In addition, both DentaPro and PeriOSM showed significant vertical bone osseointegration (unlabeled bar) compared to control. Also, PeriOSM unexpectedly showed slightly improved vertical osseointegration and significant new lateral bone growth despite only using one-third of the amount of hydroxyapatite matrix compared to DentaPro and control.

INCORPORATION BY REFERENCRE

The contents of all references, patent applications, patents, and published patent applications, as well as the Figures and the Sequence Listing, cited throughout this application are hereby incorporated by reference.

EQUIVALENTS

Those skilled in the art will recognize, or be able to ascertain using no more than routine experimentation, many equivalents to the specific embodiments of the present invention described herein. Such equivalents are intended to be encompassed by the following claims.

What is claimed:

1. A method of growing bone or inhibiting bone resorption in a subject, the method comprising administering to a site in need of bone growth and/or bone resorption inhibition in the subject an effective amount of a biocompatible composition comprising:
   (a) a biocompatible polymer matrix, wherein the polymer matrix is agarose; and
   (b) a conditioned cell medium comprising i) a cell culture medium and ii) one or more agents synthesized by and secreted from one or more cells cultured in the cell culture medium, wherein the cells are fibroblasts, dermal fibroblasts, neonatal dermal fibroblasts, osteoblasts, fibroblasts and osteoblasts cultured separately, and/or a co-culture of fibroblasts and osteoblasts.

2. The method of claim 1, wherein the cell culture medium comprises a basal cell culture medium and further comprises one or more supplements selected from the group consisting of fetal bovine serum (FBS), L-glutamine, human epidermal growth factor (EGF), basic fibroblast growth factor (bFGF), and ascorbic acid.

3. The method of claim 2, wherein the basal cell culture medium is Dulbecco's modified eagle medium (DMEM).

4. The method of claim 2 or 3, wherein the supplement is a recombinant growth factor.

5. The method of claim 4, wherein the recombinant growth factor is a human recombinant growth factor.

6. The method of claim 1, wherein the one or more agents synthesized by and secreted from one or more cells cultured in the cell culture medium comprises a growth factor.

7. The method of claim 1, wherein the one or more agents synthesized by and secreted from one or more cells cultured in the cell culture medium is selected from the group consisting of platelet-derived growth factor (PDGF), epidermal growth factor (EGF), fibroblast growth factor (FGF), basic fibroblast growth factor (bFGF), vascular endothelial growth factor (VEGF), keratinocyte growth factor (KGF), transforming growth factor alpha (TGFα), transforming growth factor beta (TGFβ), transforming growth factor beta-1 (TGFβ1), transforming growth factor beta-2 (TGFβ2), insulin-like growth factor (IGF), nerve growth factor (NGF), hepatocyte growth factor (HGF), insulin, hydrocortisone, urogastrone, platelet-derived wound healing factor (PDWHF), brain-derived neurotrophy factor (BDNF), platelet factor IV (PF IV), tumor necrosis factor (TNF), granulocyte colony stimulating factor (GCSF), colony-stimulating factors (CSF), bone morphogenetic protein (BMP), osteocalcin, osteopontin, interleukin-1, interleukin-6, interleukin-8 (IL-8), interleukin-11, and growth differentiation factor (GDF), and combinations thereof.

8. The method of claim 1, wherein the one or more agents synthesized by and secreted from one or more cells cultured in the cell culture medium is present in the conditioned medium at a concentration selected from the group consisting of at least about 2 times, about 3 times, about 4 times, about 5 times, about 6 times, about 7 times, about 8 times, about 9 times, about 10 times, about 11 times, about 12 times, about 13 times, about 14 times, about 15 times, about 16 times, about 17 times, about 18 times, about 19 times, about 20 times, about 25 times, about 30 times, about 40 times, about 50 times, about 60 times, about 70 times, about 80 times, about 90 times, and about 100 times, increased as compared to the concentration in the cell culture medium before culturing.

9. The method of claim 1, wherein the cells are cultured in the cell culture medium for at least 24 hours.

10. The method of claim 9, wherein the cells are cultured in the cell culture medium for at least 48 hours or for at least 72 hours.

11. The method of claim 1, wherein the biocompatible composition does not comprise cells.

12. The method of claim 1, wherein the conditioned cell medium is concentrated.

13. The method of claim 12, wherein the conditioned cell medium is concentrated by tangential flow filtration.

14. The method of claim 1, wherein the conditioned cell medium is present at about 50% of the volume of the biocompatible composition.

15. The method of claim 1, wherein the agarose is derived from seaweed.

16. The method of claim 1, wherein the agarose is low melting point agarose or ultra-low melting point agarose.

17. The method of claim 1, wherein the agarose is about 0.8% to about 3.0% weight to volume (w:v).

18. The method of claim 1, wherein the method enhances total osseointegration, vertical osseointegration, and/or lateral osseointegration of new bone growth at a site of bone growth and/or bone resorption inhibition.

19. The method of claim 1, wherein the subject has a bone fracture, bone deficiency, metastatic bone disease, osteoarthritis, osteoporosis, and/or osteolytic bone disease.

20. The method of claim 1, wherein bone mass is maintained or increased, bone density is maintained or increased, gum tissue is maintained or increased, or any combination thereof.

21. The method of claim 1, wherein the method further comprises administering to the subject an effective amount of a therapeutic agent that a) promotes gum and/or bone growth and/or b) inhibits gum erosion and/or bone resorption.

22. The method of claim 21, wherein administering said biocompatible composition and administering said therapeutic agent is sequential.

23. The method of claim 21, wherein administering said biocompatible composition and administering said therapeutic agent is simultaneous.

24. The method of claim 22 or 23, wherein the therapeutic agent is selected from the group consisting of bone morphogenetic factors, anti-resorptive agents, osteogenic factors, cartilage-derived morphogenetic proteins, growth hormones, estrogens, bisphosphonates, statins, differentiating factors, analgesics, anesthetics, antimicrobial agents, antibacterial agents, antiviral agents, antifungal agents, antibiotics, anti-inflammatory agents, antioxidants, antiseptic agents, immunostimulating agents, and combinations thereof.

25. The method of claim 1, wherein the biocompatible composition is topically administered to the site.

26. The method of claim 25, wherein the topical administration is selected from the group consisting of a wound dressing, surgical closure, stapling, adhesive strip, bioadhesive, or gum flap.

27. The method of claim 1, wherein the subject is a mammal, a human, a cat, a dog, a horse, or a rodent.

28. The method of claim 1, wherein the subject is an animal model of a disorder in need of periodontal i) gum and/or bone growth and/or ii) gum erosion and/or bone resorption inhibition.

* * * * *